United States Patent [19]
Abe et al.

[11] Patent Number: 5,283,384
[45] Date of Patent: Feb. 1, 1994

[54] TRACTION DRIVE FLUID, PROCESS FOR PRODUCING THE SAME AND BICYCLO OCTANE COMPOUND

[75] Inventors: Kazuaki Abe; Toshiyuki Tsubouchi, both of Sodegaura; Hitoshi Hata, Ichihara, all of Japan

[73] Assignee: Idemitsu Kosan Co., Ltd., Tokyo, Japan

[21] Appl. No.: 844,474

[22] Filed: Mar. 2, 1992

[30] Foreign Application Priority Data

Apr. 8, 1991 [JP] Japan ................................. 3-75145

[51] Int. Cl.$^5$ ..................... C07C 13/44; C07C 13/605
[52] U.S. Cl. ......................... 585/22; 585/20; 585/21; 585/350; 585/362
[58] Field of Search ............... 585/350, 361, 362, 375, 585/20, 21, 22

[56] References Cited

U.S. PATENT DOCUMENTS 3,440,894  4/1969  Hammann et al. ............ 74/200

FOREIGN PATENT DOCUMENTS

| 72204 | 4/1982 | European Pat. Off. |
| 0082967 | 7/1983 | European Pat. Off. |
| 0305807 | 3/1989 | European Pat. Off. |
| 0362673 | 4/1990 | European Pat. Off. |
| 402881 | 12/1990 | European Pat. Off. |
| 1190836 | 5/1970 | United Kingdom |

OTHER PUBLICATIONS

Rodd's Chemistry of Carbon Compounds; S. Coffey, editor, Elsevier Pub. Co., 1969, pp. 51, 108 and 117.

*Primary Examiner*—Asok Pal
*Assistant Examiner*—P. Achutamurthy
*Attorney, Agent, or Firm*—Frishauf, Holtz, Goodman & Woodward

[57] ABSTRACT

A traction drive fluid composition comprising a hydrocarbon having a bicyclo octane skeleton, such as a bicyclo(3,2,1) octane skeleton, a bicyclo(2,2,2)octane skeleton or a bicyclo(3,3,0)octane skeleton. The traction drive fluid has a low viscosity and has a high traction coefficient over a wide temperature range.

7 Claims, 21 Drawing Sheets

TRACTION DRIVE FLUID, PROCESS FOR PRODUCING THE SAME AND BICYCLO OCTANE COMPOUND

BACKGROUND OF THE INVENTION

1. Field of the Invention

The present invention relates to a traction drive fluid comprising a hydrocarbon, a process for producing the same and a bicyclo octane compound. More particularly, it is concerned with a traction drive fluid comprising hydrocarbon having good flowability at low temperatures and exhibiting high traction performance in a wide temperature range from low to high temperatures, a process for producing the same efficiently and a novel bicyclo octane compound. Further, the present invention relates to a process for improving the traction coefficient at high temperatures between at least two relatively rotatable elements in a torque transmitting relationship.

2. Description of the Related Arts

Generally, traction drive fluids are used in traction drive units (friction driving equipment utilizing rolling contact), for example, continuously variable transmission for automobiles, industrial equipment or hydraulic machines. Users have required that traction drive fluids should have a high traction coefficient and be stable with respect of heat and oxidation and their cost should be at a reasonable level, as the demands for them have been increasing.

In recent years, the attempts to construct small size and light weight traction drive units have been made for the sake of chiefly the automobile use and there have been emphasized the needs that Traction drive fluids intended for use in said units have been required to be capable of working under various different severe conditions and achieving stable and high performance, for example, a high traction coefficient, an adequate viscosity, and a high stability in heat and oxidation, in a wide temperature range from low to high temperatures, approximately $-30°$ to $140°$ C.

So far, various different traction drive fluids have been developed and disclosed, for example in Japanese Patent Publication Nos. 338/1971, 339/1971 and 44918/1986, but it has been found that none of them satisfy above-mentioned required properties and is faulty on many points. Of these traction drive fluids, for example, the compounds having a high traction coefficient at high temperatures cause a large churning loss because of the high viscosity, thus resulting in low transmission efficiency, but also having poor capability to start traction drive units at low temperatures. The other compounds of a low viscosity and therefore high transmission efficiency have a significantly low traction coefficient at high temperatures and their viscosity decrease with increasing oil temperature too much, causing trouble with respect of lubrication in traction drive units.

The present inventors have made intensive studies with a view to finding the solution of above-mentioned technical difficulties of prior arts and developing a traction drive fluid having a low viscosity and exhibiting high performance in a wide temperature range.

As the result, it has been found that above-mentioned objects can be achieved with a traction drive fluid containing a bicyclo octane skeleton as the active substance and the present invention has been completed on the basis of the finding.

SUMMARY OF THE INVENTION

An object of the present invention is to provide a traction drive fluid exhibiting excellent performance over a wide temperature range from low temperature to high temperature.

Another object of the present invention is to provide a traction drive fluid having a high traction coefficient and a low viscosity.

Another object of the present invention is to decrease the size and weight of a tractin drive unit, to lengthen its service life, and to increase its power.

Still another object of the present invention is to provide novel bicyclo octane compounds useful for a traction drive fluid.

The present invention provides a hydrocarbonic traction drive fluid containing a bicyclo octane skeleton.

The present invention also provides a process for improving the traction coefficient between at least two relatively rotatable elements in a torque transmitting relationship which comprises introducing between the tractive surfaces of said elements a traction drive fluid comprising as the active component a hydrocarbon compound having a bicyclo octane skeleton.

Moreover, the present invention provides a process for producing the hydrocarbonic traction drive fluid by using, as a starting material, bicyclo octene, a derivative thereof, bicyclo octane or a derivative thereof represented by the following general formula (I):

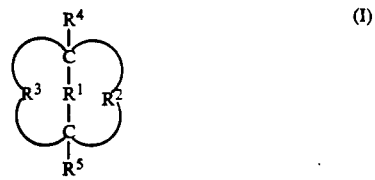

(I)

wherein $R^1$, $R^2$ and $R^3$ each represent an alkylene group having 1 to 5 carbon atoms, an alkenylene group having 2 to 5 carbon atoms or an single bond; they may each have a substituent; the total carbon atoms in $R^1$, $R^2$ and $R^3$ excluding their substituents are 6; $R^4$ and $R^5$ and said substituents each represent an alkyl group having 1 to 4 carbon atoms, an alkenyl group having 2 to 4 carbon atoms, an alkylidene group having 1 to 4 carbon atoms (provided that the alkyl group, the alkenyl group and the alkylidene group may each have been substituted with a hydroxyl group or a halogen atom), a hydroxyl group, a hydrogen atom or a halogen atom; and the total number of carbon atoms is from 8 to 14 in the formula hereof, dimerizing or co-dimerizing said starting material with an acid catalyst or subjecting said starting material to the Friedel-Crafts reaction and hydrogenating the reaction product.

The present invention also provides a novel bicyclo octane compound represented by the following general formula (III), (IV), (V), (VI), (VII), (VIII), (IX) or (X):

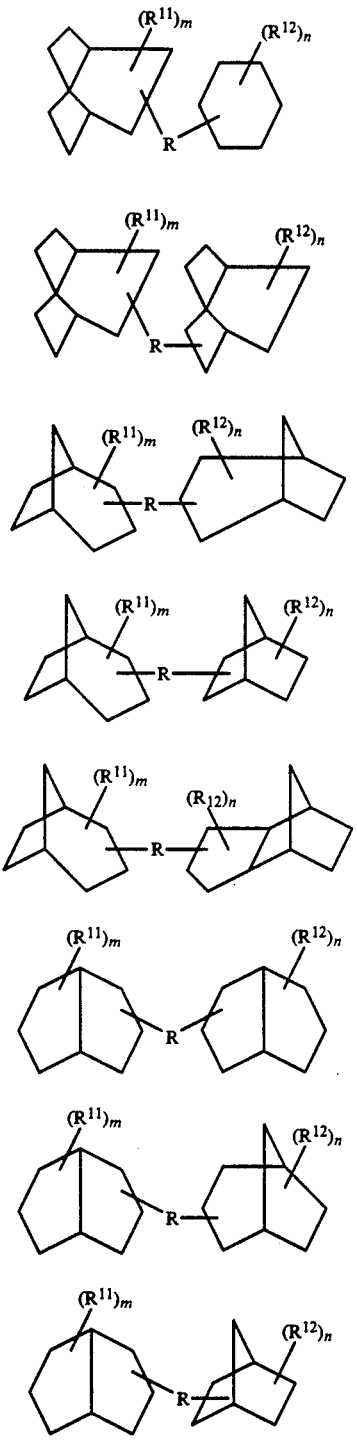

(III)

(IV)

(V)

(VI)

(VII)

(VIII)

(IX)

(X)

wherein $R^{11}$ and $R^{12}$ each represent a hydrogen atom, a methyl group or an ethyl group; m and n each represent an integer of 1 to 4; R represents a single bond or an alkylene group having 1 to 2 carbon atoms; and said alkylene group may have been substituted with an alkyl group having 1 to 2 carbon atoms.

BRIEF DESCRIPTION OF THE DRAWINGS

In FIGS. 1 to 3, the symbols mean as follows:
1 Example 1
2 Example 2
3 Comparative Example 1
4 Example 3
5 Example 4
6 Example 7
7 Comparative Example 2
8 Example 5
9 Example 6
10 Comparative Example 3

DESCRIPTION OF THE PREFERRED EMBODIMENTS

Figure 1:
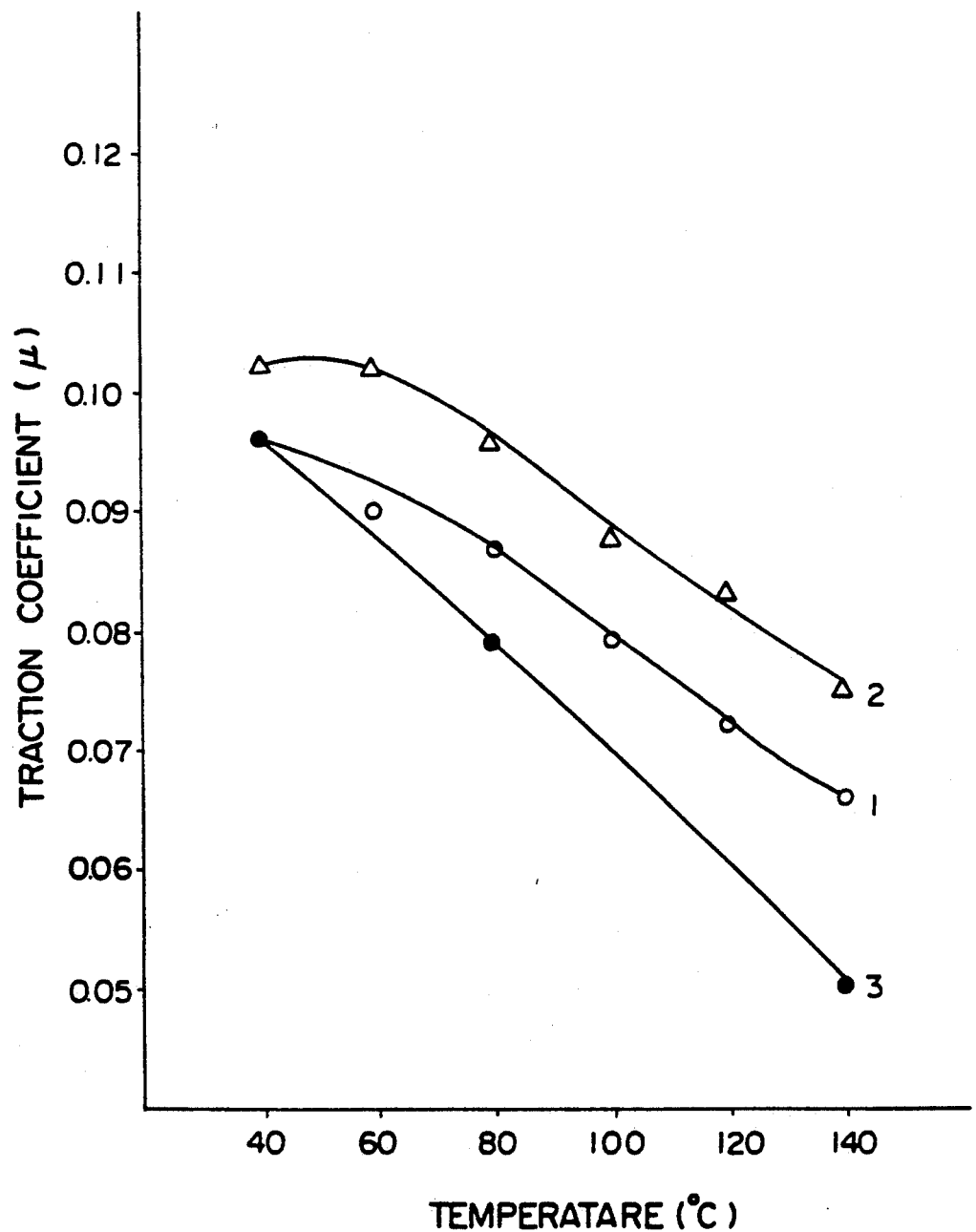
FIG. 1 is a graph showing temperature dependence of the traction coefficient in connection with the compounds of Example 1, Example 2 and Comparative Example 1.

The traction drive fluid of hydrocarbon of the present invention contains a bicyclo octane skeleton. Examples of said bicyclo octane skeleton include a whole assortment of bicyclo[3.2.1]octane skeleton, bicyclo[2.2.2]octane skeleton and bicyclo[3.3.0]octane skeleton. The compounds having these bicyclo octane skeletons include bicyclo octane and/or derivatives thereof and bicyclo octene and/or derivatives thereof (hereinafter sometimes referred to respectively as bicyclo octanes and as bicyclo octenes) and the like.

According to the present invention, a hydrogenated dimer of bicyclo octenes or bicyclo octanes, or a hydrogenated co-dimer of bicyclo octanes and bicyclo octanes is preferably used for the traction drive fluid. Various compounds can be mentioned as bicyclo octanes or bicyclo octenes, including those represented by the above general formula (I). In the general formula (I) wherein the total number of carbon atoms should be from 8 to 14, $R^1$, $R^2$ and $R^3$ each represent an alkylene group having 1 to 5 carbon atoms (methylene group, ethylene group, trimethylene group and the like), an alkenylene group having 2 to 5 carbon atoms in the case of bicyclo octenes (vinylene group, propenylene group and the like) or a single bond (namely, a symbol of bonding two carbon atoms (C) in the formula), and each of them may have a substituent. The total carbon atoms in $R^1$, $R^2$ and $R^3$ excluding their substituents are 6, in other words, the carbon atoms of $R^1$, $R^2$ and $R^3$, plus two other carbon atoms (C) in the formula, total 8 (octane or octene). Further, $R^4$ and $R^5$ and said substituents each represent an alkyl group having 1 to 4 carbon atoms, an alkenyl group having 2 to 4 carbon atoms, an alkylidene group having 1 to 4 carbon atoms (provided that the alkyl group, the alkenyl group and the alkylidene group may each have been substituted with a hydroxyl group or a halogen atom) or a hydroxyl group, a hydrogen atom or a halogen atom.

Specific examples of these compounds having the bicyclo octane skeleton (bicyclo octanes, bicyclo octenes and the like) are (A) bicyclo[2.2.2]octanes or octenes including 2-vinyl-bicyclo[2.2.2]octane, 2-ethylidene-bicyclo[2.2.2]octane, 2-(1-hydroxyethyl)-bicyclo[2.2.2]octane, 2-methylene-bicyclo[2.2.2]octane, bicyclo[2.2.2]-2-octene, 2-methyl-bicyclo[2.2.2]-2-octene, 2-hydroxymethyl-bicyclo[2.2.2]octane, 2,3-dimethyl-bicyclo[2.2.2]-2-octene and 2-methyl-3-methylene-bicyclo[2.2.2]octane and (B) bicyclo[3.2.1]octanes or octenes including 4-methyl-bicyclo[3.2.1]-2-octene, bicyclo[3.2.1]-2-octene and 2-methyl-bicyclo[2.2.1]-2-octene. Further, as bicyclo[3.3.0]octanes or octenes, bicyclo[3.3.0]-2-octene, 6-methyl-bicyclo[3.3.0]-2-octene and 3-methyl-bicyclo[3.3.0]-2-octene can be mentioned.

The traction drive fluid of the present invention may contain a hydrogenated dimer or co-dimer of above-mentioned bicyclo octanes and/or bicyclo octenes. Also acceptable is a hydrogenated dimer or co-dimer of bicyclo octanes or bicyclo octenes combined with bicyclo heptane or a derivative thereof, bicyclo heptene or a derivative thereof or other hydrocarbon compounds.

Other than those above-mentioned compounds, for example, bicyclo heptane or a derivative thereof and bicyclo heptene or a derivative thereof (hereinafter referred to respectively as bicyclo heptanes and as bicyclo heptenes) represented by the following general formula (II) may as well be mentioned as the starting material for producing the co-dimer to be used in the present invention:

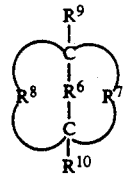
(II)

wherein $R^6$, $R^7$ and $R^8$ each represent an alkylene group having 1 to 4 carbon atoms, an alkenylene group having 2 to 4 carbon atoms or a single bond; they may each have a substituent; the carbon atoms total 5 in $R^6$, $R^7$ and $R^8$ excluding said substituents; $R^9$ and $R^{10}$ and said substituents each represent an alkyl group having 1 to 4 carbon atoms, an alkenyl group having 2 to 4 carbon atoms, an alkylidene group having 1 to 4 carbon atoms (provided that the alkyl group, the alkenyl group and the alkylidene group may each have been substituted with a hydroxyl group or a halogen atom) or a hydroxyl group, a hydrogen atom or a halogen atom; and the total number of carbon atoms is from 7 to 14 in the formula hereof. Specific examples of bicyclo heptanes or bicyclo heptenes represented by said general formula (II) are (C) bicyclo[2.2.1]heptanes or heptenes including bicyclo[2.2.1]-2-heptene, 2-methyl-bicyclo[2.2.1]-2-heptene, 2-methylenebicyclo[2.2.1]heptane, 2-vinyl-bicyclo[2.2.1]heptane, 2-ethylidene-bicyclo[2.2.1]heptane, 2-isopropyl-bicyclo[2.2.1]-2-heptene, 2-isopropylidene-bicyclo[2.2.1]heptane, 2,2-dimethyl-bicyclo[2.2.1]-2-heptene, 3-methyl-2-methylene-bicyclo[2.2.1]heptane, 2-hydroxymethyl-3-methyl-bicyclo[2.2.1]heptane and 2-hydroxymethyl-bicyclo[2.2.1]heptane. Furthermore, bicyclo octenes or bicyclo octanes represented by above-mentioned general formula (I) also can be obtained by selecting bicyclo heptanes or bicyclo heptenes having the total carbon atoms of 8 to 14 from those represented by above-mentioned general formula (II) and isomerizing them with an acid catalyst.

Various other types of hydrocarbons having 5 to 14 carbon atoms can be used as the starting material for producing co-dimers of bicyclo octanes and bicyclo octenes, including dihydrodimethyldicyclopentadiene, dihydrodicyclopentadiene, dicyclopentadiene, dimethyldicyclopentadiene, cyclopentene, cyclohexene, styrene, α-methylstyrene and vinylnaphthalene. Further, (D) aromatic hydrocarbons can be used herein, including benzene, toluene, o-xylene, m-xylene, p-xylene, pseudocumene, durene, naphthalene and tetralin.

The above mentioned starting materials of the present invention can be subjected to a dimerization or co-dimerization reaction, including a dehydration dimerization and a isomerization dimerization, according to the combinations such as A x A, A x B, B x B, A x C, A x D, B x C and B x D. As used herein, the symbol x means the (co-) dimerization reaction. Further, the combinations also include (C→A) x C, (C→A) x (C→A), (C→B) x C, (C→B) x (C→B), (C→A) x (C→B), (C→A) x D and (C→B) x D. As used herein, the symbol C→A means that C is isomerized to A and that of C→B means that C is isomerized to B.

The methods as described above are efficient to produce traction drive fluids according to the present invention. The above mentioned dimerization or co-dimerization reaction is conducted in the presence of a catalyst by adding a solvent or reaction promoter if necessary, or is conducted by the Friedel-Crafts reaction. Various different catalysts can be put to use therefor, but usually acid catalysts are used.

Examples of the acid catalyst (or Friedel-Crafts catalyst) include clays such as activated clay and acid clay, mineral acids such as sulfuric acid and hydrochloric acid, organic acids such as p-toluenesulfonic acid and triflic acid, Lewis acids such as aluminum chloride, ferric chloride, stannic chloride, titanium trichloride, titanium tetrachloride, boron trifluoride, hydrogen fluoride, boron tribromide, aluminum bromide, gallium chloride and gallium bromide, and solids acids such as zeolite, silica, alumina, silica-alumina and cationic ion exchange resin and heteropolyacid. Among these compounds, an acid catalyst considered appropriate is selected by the criterion that it is easy to handle, its cost is at a reasonable level and so on. The amount of these catalysts to be used is not limited, but usually it is 0.1 to 100% by weight, preferably 1 to 20% by weight on the basis of the starting material such as bicyclo octanes.

Solvents are not necessarily essential when bicyclo octanes and the like are subjected to above-mentioned dimerization or co-dimerization reaction, but it is preferable to use them in order to make the handling of bicyclo octanes or catalysts easier during the reaction or adjust progresses of the reaction. A wide variety of compounds can be freely used as the solvent, including saturated hydrocarbons such as n-pentane, n-hexane, heptane, octane, nonane, decane cyclopentane, cyclohexane, methylcyclohexane and decalin. Further, aromatic hydrocarbons such as benzene, toluene and xylene, and tetralin may as well be used in the presence of a catalyst less active to promote the reaction like clay. Mineral oils (150 neutral oil, 500 neutral oil) can be used as the solvent herein as well.

Reaction promoters are used particularly to increase the selectivity of the dimerization and co-dimerization reaction, aimed at causing bicyclo octanes to react properly if necessary, and their amount is ordinarily in a range of 0.1 to 100% by weight, preferably from 0.5 to 20% by weight on the basis of the amount of catalysts. Specific examples of reaction promoters include carboxylic acid such as acetic acid, acid anhydride such as acetic anhydride and phthalic anhydride, cyclic esters such as γ-butyrolactone and valerolactone, glycols such as ethylene glycol, esters such as ethyl acetate, ketones such as mesityl oxide, aldehydes such as formalin and acetoaldehyde, cellosolve and water.

The above mentioned reaction is carried out generally in a temperature range of from −30° to 300° C. and the appropriate reaction conditions are anywhere within that range depending upon the kind of catalysts and additives to be used. For example, when clays or zeolites are used as a catalyst, the reaction is carried out in a range of from room temperature to 250° C., preferably 60° C. or higher and with other catalysts from −30° to 100° C., preferably from 0° to 60° C.

According to the process of the present invention, bicyclo octanes or bicyclo octenes are dimerized or co-dimerized according to above-mentioned procedure, followed by hydrogenating the obtained reaction product. Either the hydrogenation is carried out with respect to all of the reaction product from the dimerization or co-dimerization of bicyclo octanes and like, or the fractionation or distillation is conducted for a part of said reaction product.

Said hydrogenation is conducted in the presence of a catalyst as in the case of dimerization or co-dimerization, and examples of said catalyst include a catalyst for hydrogenation which contains at least a metal selected from nickel, ruthenium, palladium, platinum, rhodium, iridium, copper, chromium, molybdenum, cobalt, tungsten and the like. The amount of the catalyst to be used is not limited, but usually it is 0.1 to 100% by weight, preferably 1 to 10% by weight based on the amount of dimerized or co-dimerized product of said bicyclo octanes and the like.

Further, the hydrogenation reaction proceeds in the absence of a solvent in the same manner of said dimerization or co-dimerization, but the use of solvents is acceptable as well. Examples of the solvent to be used herein include almost all classes of liquid saturated hydrocarbons such as n-pentane, n-hexane, heptane, octane, nonane, decane, dodecane, cyclopentane, cyclohexane and methylcyclohexane. Moreover, aromatics, olefins, alcohols, ketones and ethers may as well be used herein if they are in a liquid form, and particularly a saturated hydrocarbon is preferred. The reaction temperature for hydrogenation is in a range of from room temperature to 300° C., preferably from 40° C. to 200° C., while the reaction pressure is in a range of from atmospheric pressure to 200 kg/cm$^2$G, preferably from atmospheric pressure to 150 kg/cm$^2$G. Said hydrogenation is carried out in accordance with substantially the same procedure as in the ordinary hydrogenation processes.

According to the present invention, the novel bicyclo octane compounds represented by above-mentioned general formulae from (III) to (X) can be obtained by said dimerization and co-dimerization. Here follow specific examples of the novel compounds: those represented by the general formula (III) include 1-(bicyclo[2.2.2]-2-octyl)-1-(trimethylcyclohexyl)-ethane, 1-(bicyclo[2.2.2]-2-octyl)-1-(trimethylcyclohexyl)-methane, 1-[3-methyl-bicyclo[2.2.2]-2-octyl)-1-(decalyl)-ethane, 1-[3-methyl-bicyclo[2.2.2]-2-octyl)-1-(decalyl)-methane, (bicyclo[2.2.2]-2-octyl)-trimethylcyclohexane and (bicyclo[2.2.2]-2-octyl)-decalin.

Specific examples of the compounds represented by the general formula (IV) include 1,1-bis(bicyclo[2.2.2]-2-octyl)-methane, 1,1-bis(bicyclo[2.2.2]-2-octyl)-ethane, bis(bicyclo[2.2.2]-2-octyl), 1-(2-methyl-bicyclo[2.2.2]-2-octyl)-1-(bicyclo[2.2.2]-2-octyl)-methane, 1-(2-methyl-bicyclo[2.2.2]-2-octyl)-1-(bicyclo[2.2.2]-2-octyl)-ethane, 1-(2, 3-dimethyl-bicyclo[2.2.2]-2-octyl)-1-(3-methyl-bicyclo[2.2.2]-2-octyl)-methane and 1-(2, 3-dimethyl-bicyclo[2.2.2]-2-octyl)-1-(3-methyl-bicyclo[2.2.2]-2-octyl)-ethane.

Specific examples of the compounds represented by the general formula (V) include 2-(bicyclo[3.2.1]-2-octyl)-bicyclo[3.2.1]octane, 3-(bicyclo[3.2.1]-2-octyl)-bicyclo[3.2.1]octane, bis(bicyclo[3.2.1]-2-octyl), bis(bicyclo[3.2.1]-3-octyl), bis(4-methyl-bicyclo[3.2.1]-2-octyl), bis(4-methyl-bicyclo[3.2.1]-3-octyl), 1-(2-methyl-bicyclo[3.2.1]-2-octyl)-1-(bicyclo[3.2.1]-2-octyl)-methane, 1-(2-methyl-bicyclo[3.2.1]-2-octyl)-1-(bicyclo[3,2,1]-2-octyl)-ethane, 2-(2-methylbicyclo[3.2.1]-2-octyl)-bicyclo[3.2.1]octane, 3-(2-methylbicyclo[3.2.1]-2-octyl)-bicyclo[3.2.1]octane, 2-(4-methylbicyclo[3.2.1]-2-octyl)-bicyclo[3.2.1]octane, 2-(4-methylbicyclo[3.2.1]-3-octyl)-bicyclo[3.2.1]octane, 3-(4-methylbicyclo[3.2.1]-2-octyl)-bicyclo[3.2.1]octane, 3-(4-methylbicyclo[3.2.1]-3-octyl)-bicyclo[3.2.1]octane, 2-(4-methylbicyclo[3.2.1]-2-octyl)-(2-methylbicyclo[3.2.1]octane), 2-(4-methylbicyclo[3.2.1]-3-octyl)-(2-methylbicyclo[3.2.1]octane), 3-(4-methylbicyclo[3.2.1]-2-octyl)-(2-methylbicyclo[3.2.1]octane) and 3-(4- methylbicyclo[3.2.1]-3-octyl)-(2-methylbicyclo[3.2.1]octane).

Specific examples of the compounds represented by the general formula (VI) include 2-(bicyclo[3.2.1]-2-octyl)-bicyclo[2.2.1]heptane, 2-(2-methyl-bicyclo[3.2.1]-3-octyl)-(2,3-dimethylbicyclo[2.2.1]heptane), 2-(2-methyl-bicyclo[3.2.1]-4-octyl)-(2,3-dimethylbicyclo[2.2.1]heptane), 2-(2-methyl-bicyclo[3.2.1]-3-octyl)-(2-methylbicyclo[2.2.1]heptane, 2-(2-methyl-bicyclo[3.2.1]-4-octyl)-(2-methylbicyclo[2.2.1]heptane), 2-(2-methyl-bicyclo[3.2.1]-3-octyl)-(3-methylbicyclo[2.2.1]heptane), 2-(2-methyl-bicyclo[3.2.1]-4-octyl)-(3-methylbicyclo[2.2.1]heptane), 1-(2-methyl-bicyclo[3.2.1]-3-octyl)-1-(2-methylbicyclo[2.2.1]-2-heptyl)methane, 1-(2-methyl-bicyclo[3.2.1]-4-octyl)-1-(2-methylbicyclo[2.2.1]-2-heptyl)methane, 1-(2-methyl-bicyclo[3.2.1]-3-octyl)-1-(2-methylbicyclo[2.2.1]-2-heptyl)ethane, 1-(2-methyl-bicyclo[3.2.1]-4-octyl)-1-(2-methylbicyclo[2.2.1]-2-heptyl)ethane, 1-(2-methyl-bicyclo[3.2.1]-3-octyl)-1-(2-methylbicyclo[2.2.1]-3-heptyl)methane, 1-(2-methyl-bicyclo[3.2.1]-4-octyl)-1-(2-methylbicyclo[2.2.1]-3-heptyl)methane, 1-(2-methyl-bicyclo[3.2.1]-3-octyl)-1-(2-methylbicyclo[2.2.1]-3-heptyl)ethane, 1-(2-methyl-bicyclo[3.2.1]-4-octyl)-1-(2-methylbicyclo[2.2.1]-3-heptyl)ethane, 1-(2-methyl-bicyclo[3.2.1]-3-octyl)-1-(bicyclo[2.2.1]-2-heptyl)methane, 1-(2-methyl-bicyclo[3.2.1]-4-octyl)-1-(bicyclo[2.2.1]-2-heptyl)methane, 1-(2-methyl-bicyclo[3.2.1]-3-octyl)-1-(bicyclo[2.2.1]-2-heptyl)ethane, 1-(2-methyl-bicyclo[3.2.1]-4-octyl)-1-(bicyclo[2.2.1]-2-heptyl)ethane, 1-(bicyclo[3.2.1]-2-octyl)-1-(bicyclo[2.2.1]-2-heptyl)methane, 1-(bicyclo[3.2.1]-3-octyl)-1-(bicyclo[2.2.1]-2-heptyl)methane, 1-(bicyclo[3.2.1]-2-octyl)-1-(bicyclo[2.2.1]-2-heptyl)ethane and 1-(bicyclo[3.2.1]-3-octyl)-1-(bicyclo[2.2.1]-2-heptyl)ethane.

Specific examples of the compounds represented by the general formula (VII) include 3-(bicyclo[3.2.1]-2-octyl)-tricyclo[5.2.1.0$^{2.6}$]decane, 4-(bicyclo[3.2.1]-2-octyl)-tricyclo[5.2.1.0$^{2.6}$]decane, 3-(2-methylbicyclo[3.2.1]-3-octyl)-tricyclo[5.2.1.0$^{2.6}$]decane, 3-(2-methylbicyclo[3.2.1]-4-octyl)-tricyclo[5.2.1.0$^{2.6}$]decane, 4-(2-methylbicyclo[3.2.1]-3-octyl)-tricyclo[5.2.1.0$^{2.6}$]decane, 4-(2-methylbicyclo[3.2.1]-4-octyl)-tricyclo[5.2.1.0$^{2.6}$]decane, 1-(bicyclo[3.2.1]-2-octyl)-1-(tricyclo[5.2.1.0$^{2.6}$]decyl)methane, 1-(bicyclo[3.2.1]-2-octyl)-1-(tricyclo[5.2.1.0$^{2.6}$]-4-decyl)methane, 1-(bicyclo[3.2.1]-3-octyl)-1-(tricyclo[5.2.1.0$^{2.6}$]-3-decyl)methane, 1-(bicyclo[3.2.1]-3-octyl)-1-(tricyclo[5.2.1.0$^{2.6}$]-4-decyl)methane, 1-(bicyclo[3.2.1]-2-octyl)-1-(tricyclo[5.2.1.0$^{2.6}$]-3-decyl)ethane, 1-(bicyclo[3.2.1]-2-octyl)-1-(tricyclo[5.2.1.0$^{2.6}$]-4-decyl)ethane, 1-(bicyclo[3.2.1]-3-octyl)-1-(tricyclo[5.2.1.0$^{2.6}$]-3-decyl)ethane and 1-(bicyclo[3.2.1]-3-octyl)-1-(tricyclo[5.2.1.0$^{2.6}$]-4-decyl)ethane.

Specific examples of the compounds represented by the general formula (VIII) include 2-(bicyclo[3.3.0]-2-octyl)-bicyclo[3.3.0]octane, 3-(bicyclo[3.3.0]-2-octyl)-bicyclo[3.3.0]octane, bis(bicyclo[3.3.0]-2-octyl), bis(bicyclo[3.3.0]-3-octyl), bis(4-methyl-bicyclo[3.3.0]-2-octyl), bis(4-methyl-bicyclo[3.3.0]-3-octyl), 1-(2-methyl-bicyclo[3.3.0]-2-octyl)-1-(bicyclo[3.3.0]-2-octyl)methane, 1-(2-methyl-bicyclo[3.3.0]-2-octyl)-1-(bicyclo[3.3.0]-2-octyl)-ethane, 2-(2-methylbicyclo[3.3.0]-2-octyl)-bicyclo[3.3.0]octane, 3-(2-methylbicyclo[3.3.0]-2-octyl)-bicyclo[3.3.0]octane, 2-(4-methylbicyclo[3.3.0]-2-octyl)-bicyclo[3.3.0]octane, 2-(4-methylbicyclo[3.3.0]-3-octyl)-bicyclo[3.3.0]octane, 3-(4-methylbicyclo[3.3.0]-3-octyl)-bicyclo[3.3.0]octane, 2-(4-methylbicyclo[3.3.0]-2-octyl)-(2-methylbicyclo[3.3.0]octane), 2-(4-methylbicyclo[3.3.0]-3-octyl)-(2-methylbicyclo[3.3.0]octane), 3-(4-methylbicyclo[3.3.0]-2-octyl)-(2-methylbicyclo[3.3.0]octane) and 3-(4-methylbicyclo[3.3.0]-3-octyl)-(2-methylbicyclo[3.3.0]octane).

Specific examples of the compounds represented by the general formula (IX) include 2-(bicyclo[3.3.0]-2-octyl)-bicyclo[3.2.1]octane, 3-(bicyclo[3.3.0]-2-octyl)-bicyclo[3.2.1]octane, 1-(2-methyl-bicyclo[3.3.0]-2-octyl)-1-(bicyclo[3.2.1]-2-octyl)-methane, 1-(2-methylbicyclo[3.3.0]-2-octyl)-1-(bicyclo[3.2.1]-2-octyl)-ethane, 2-(2-methylbicyclo[3.3.0]-2-octyl)-bicyclo[3.2.1]octane, 3-(2-methylbicyclo[3.3.0]-2-octyl)-bicyclo[3.2.1]octane, 2-(4-methylbicyclo[3.3.0]-2-octyl)-bicyclo[3.2.1]octane, 2-(4-methylbicyclo[3.3.0]-3-octyl)-bicyclo[3.2.1]octane, 3-(4-methylbicyclo[3.3.0]-2-octyl)-bicyclo[3.2.1]octane, 3-(4-methylbicyclo[3.3.0]-3-octyl)-bicyclo[3.2.1]octane, 2-(4-methylbicyclo[3.3.0]-2-octyl)-(2-methylbicyclo[3.2.1]octane), 2-(4-methylbicyclo[3.3.0]-3-octyl)-(2-methylbicyclo[3.2.1]octane), 3-(4-methylbicyclo[3.3.0]-2-octyl)-(2-methylbicyclo[3.2.1]octane) and 3-(4-methylbicyclo[3.3.0]-3-octyl)-(2-methylbicyclo[3.2.1]octane.

Specific examples of the compounds represented by the general formula (X) include 2-(bicyclo[3.3.0]-2-octyl)-bicyclo[2.2.1]heptane, 2-(2-methyl-bicyclo[3.3.0]-3-octyl)-(2,3-dimethylbicyclo[2.2.1]heptane), 2-(2-methyl-bicyclo[3.3.0]-4-octyl)-(2,3-dimethylbicyclo[2.2.1]heptane), 2-(2-methyl-bicyclo[3.3.0]-3-octyl)-(2-methylbicyclo[2.2.1]heptane), 2-(2-methyl-bicyclo[3.3.0]-4-octyl)-(2-methylbicyclo[2.2.1]heptane, 2-(2-methyl-bicyclo[3.3.0]-3-octyl)-(3-methylbicyclo[2.2.1]heptane), 2-(2-methyl-bicyclo[3.3.0]-4-octyl)-(3-methylbicyclo[2.2.1]heptane), 1-(2-methyl-bicyclo[3.3.0]-3-octyl)-1-(2-methylbicyclo[2.2.1]-2-heptyl)methane, 1-(2-methyl-bicyclo[3.3.0]-4-octyl)-1-(2-methylbicyclo[2.2.1]-2-heptyl)methane, 1-(2-methyl-bicyclo[3.3.0]-3-octyl)-1-(2-methylbicyclo[2.2.1]-2-heptyl)ethane, 1-(2-methyl-bicyclo[3.3.0]-4-octyl)-1-(2-methylbicyclo[2.2.1]-2-heptyl)ethane, 1-(2-methyl-bicyclo[3.3.0]-3-octyl)-1-(2-methylbicyclo[2.2.1]-3-heptyl)methane, 1-(2-methyl-bicyclo[3.3.0]-4-octyl)-1-(2-methylbicyclo[2.2.1]-3-heptyl)methane, 1-(2-methyl-bicyclo[3.3.0]-3-octyl)-1-(2-methylbicyclo[2.2.1]-3-heptyl)ethane, 1-(2-methyl-bicyclo[3.3.0]-4-octyl)-1-(2-methylbicyclo[2.2.1]-3-heptyl)ethane, 1-(2-methyl-bicyclo[3.3.0]-3-octyl)-1-(bicyclo[2.2.1]-2-heptyl)methane, 1-(2-methyl-bicyclo[3.3.0]-4-octyl)-1-(bicyclo[2.2.1]-2-heptyl)methane, 1-(2-methyl-bicyclo[3.3.0]-3-octyl)-1-(bicyclo[2.2.1]-2-heptyl)ethane, 1-(2-methyl-bicyclo[3.3.0]-4-octyl)-1-(bicyclo[2.2.1]-2-heptyl)ethane, 1-(bicyclo[3.3.0]-2-octyl)-1-(bicyclo[2.2.1]-2-heptyl)methane, 1-(bicyclo[3.3.0]-3-octyl)-1-(bicyclo[2.2.1]-2-heptyl)methane, 1-(bicyclo[3.3.0]-2-octyl)-1-(bicyclo[2.2.1]-2-heptyl)ethane and 1-(bicyclo[3.3.0]-3-octyl)-1-(bicyclo[2,2,1]-2-heptyl)ethane.

Meanwhile, trimers or higher polymerization products formed as a by-product during the processes for dimerization or codimerization reaction can be subjected to hydrogenation so as to use as a viscosity adjuster or traction coefficient adjuster.

The viscosity adjuster and traction coefficient adjuster are prepared by the process either (1) for distilling said by-products to separate from the dimer, hydrogenating and blending them or (2) for hydrogenating the dimer and higher polymerization products and subjecting the obtained hydrogenation product to fractional distillation or mixing to obtain the desired properties. The hydrogenation may be dispensed with if the amount of higher polymerization products is insignificant, but these adjusters are preferably a hydrogenated product if the stability in heat and oxidation is important.

The hydrogenated dimer or co-dimer according to the present invention, that is, the hydrocarbon compound having the bicyclo octane skeleton can be used as a traction drive fluid singly or in the form of a mixture with other traction drive fluids if the need arises. In the case of a mixture, the content of hydrogenated dimer (hydrocarbon having the bicyclo octane skeleton) is not subject to any limitation and is selected at discretion depending upon the kind of said hydrogenated dimer and other traction drive fluids to be incorporated, but it is preferable that a hydrogenated dimer is contained in an amount of at least 5% by weight, preferably 30% by weight or more in terms of the quantity of the traction drive fluid as a whole.

Meanwhile, the traction drive fluid of the present invention can form said mixture with various different other traction drive fluids including even oils whose traction performance is too poor to be used singly not to mention conventionally established traction drive fluids. Examples of these oils are a wide variety of liquids, including mineral oil such as paraffinic mineral oil, naphthenic mineral oil and intermediate mineral oil, alkylbenzene, polybutene, poly α-olefin, synthetic naphthene, ester, ether and the like. Of them, alkylbenzene, polybutene and synthetic naphthene are preferred. Synthetic naphthene includes an an alkane derivative having 2 or more cyclohexane rings, alkane derivative having one or more each of decalin rings and cyclohexane rings, an alkane derivative having 2 or more decalin rings, a compound having a structure wherein 2 or more cyclohexane rings or decalin rings are directly bonded, an alkane derivative having 2 or more norbornane rings and a compound having a structure wherein 2 or more norbornane rings are directly bonded. Specific examples of these types of synthetic naphthenes include 1-cyclohexyl-1-decalylethane, 1,3-dicyclohexyl-3-methylbutane, 2,4-dicyclohexylpentane, 1,2-bis(methylcyclohexyl)-2-methylpropane, 1,1-bis(methylcyclohexyl)-2-methylpropane, 2,4-dicyclohexyl-2-methylpentane, and 1,3-bis(bicyclo[2.2.1]heptyl)butane.

The traction drive fluid of the present invention is prepared by using a hydrogenated hydrocarbon having a bicyclo octane skeleton as the essential component and, as the case may be, incorporating other fluids (traction drive fluids and the like). Besides, a variety of additives can be incorporated therein if need be, including antioxidants, rust inhibitors, detergent dispersants, pour point depressants, viscosity index improvers, extreme pressure agents, antiwear agents, fatigue preventing agents, antifoam agents, oiliness improvers and colorants.

As heretofore stated, the hydrocarbon traction drive fluid having a bicyclo octane skeleton is excellent at flowability with respect of low temperatures, having a high traction coefficient in a wide temperature range from room temperature to high temperatures and besides having a low viscosity, producing insignificant churning loss and thus achieving high transmission efficiency.

Therefore, the traction drive fluid of the present invention is very useful for small size and light weight traction drive units with a long lifetime and a large output and will find its place in a wide field from a continuously variable transmission for automobiles and industrial equipment to hydraulic machines and a variety of other appliances.

The present invention will now be described in greater detail referring to the following examples and comparative examples.

EXAMPLE 1

(1) The preparation of 2-(1-hydroxyethyl)bicyclo[2.2.2]octane

In a 2 liter stainless steel autoclave, 400 g of 1,3-cyclohexadiene and 420 ml of methyl vinyl ketone were placed and stirred at 160° C. for 5 hours. The pressure was caused to rise to a maximum of 6 kg/cm$^2$G and go down to a minimum of 1.5 kg/cm$^2$G.

Said reaction products were cooled to room temperature, and the compounds obtained therefrom were analyzed with the nuclear magnetic resonance spectrum (NMR), the infrared absorption spectrum (IR) and the mass spectrum (MS), resulting in the finding that the so obtained reaction product was 2-acetylbicyclo[2.2.2]-5-octene.

To the autoclave content, 20 g of 5% ruthenium/carbon catalyst (supplied by N.E. Chemcat Corp.) was added and the resulting mixture was hydrogenated under the conditions of a hydrogen pressure of 60 kg/cm$^2$G, a reaction temperature of 170° C. and a reaction time of 3 hours.

After the absorption of hydrogen was stopped, stirring was discontinued, the reaction mixture was cooled to room temperature, the catalyst was removed therefrom and the residue was distilled to obtain 750 cc of product which is one peak in gas chromatography (GC).

The so obtained reaction product was analyzed with NMR, IR and MS, resulting in a finding of 2-(1-hydroxyethyl)bicyclo[2.2.2]octane.

(2) The preparation of a hydrogenated product from the compound obtained in (1) above and the Friedel-Crafts reactant of 1,2,4-trimethylbenzene In a 2 liter four neck flask equipped with a thermometer and a hydrogen chloride gas trap, 500 ml of 1,2,4-trimethylbenzene and 150 ml of titanium tetrachloride were placed and 150 ml of 2-(1-hydroxyethyl)bicyclo[2.2.2]octane obtained in (1) above was dropped therein over 30 minutes with stirring at room temperature. The so obtained mixture was maintained at 30° C. in an ice-cold water bath and further stirred for 30 minutes. After the evolution of hydrogen chloride gas was stopped, the content of the flask was poured into 1 liter of ice-cold water to stop the reaction. The mixture was stirred well in the ice-cold water, and an organic layer produced therein was washed twice with 200 ml of 2N NaOH aqueous solution, followed by washing twice with 200 ml of water. The so treated organic layer was dried with anhydrous MgSO$_4$ and distilled to obtain 180 g of a fraction having a boiling point of 150° to 160° C./2 mmHg. The analysis with NMR and MS resulted in a finding that the so obtained reaction product was 1-(2-bicyclo[2.2.2]octyl)-1-(trimethylphenyl)-ethane.

Said reaction product was placed in a 1 liter autoclave, 20 g of 5% ruthenium/carbon catalyst and 300 ml of methylcyclohexane as the solvent were added and the resulting mixture was hydrogenated under the conditions of a hydrogen pressure of 80 kg/cm$^2$G, a reaction temperature of 200° C. and a reaction time of 6 hours.

Figure 4:
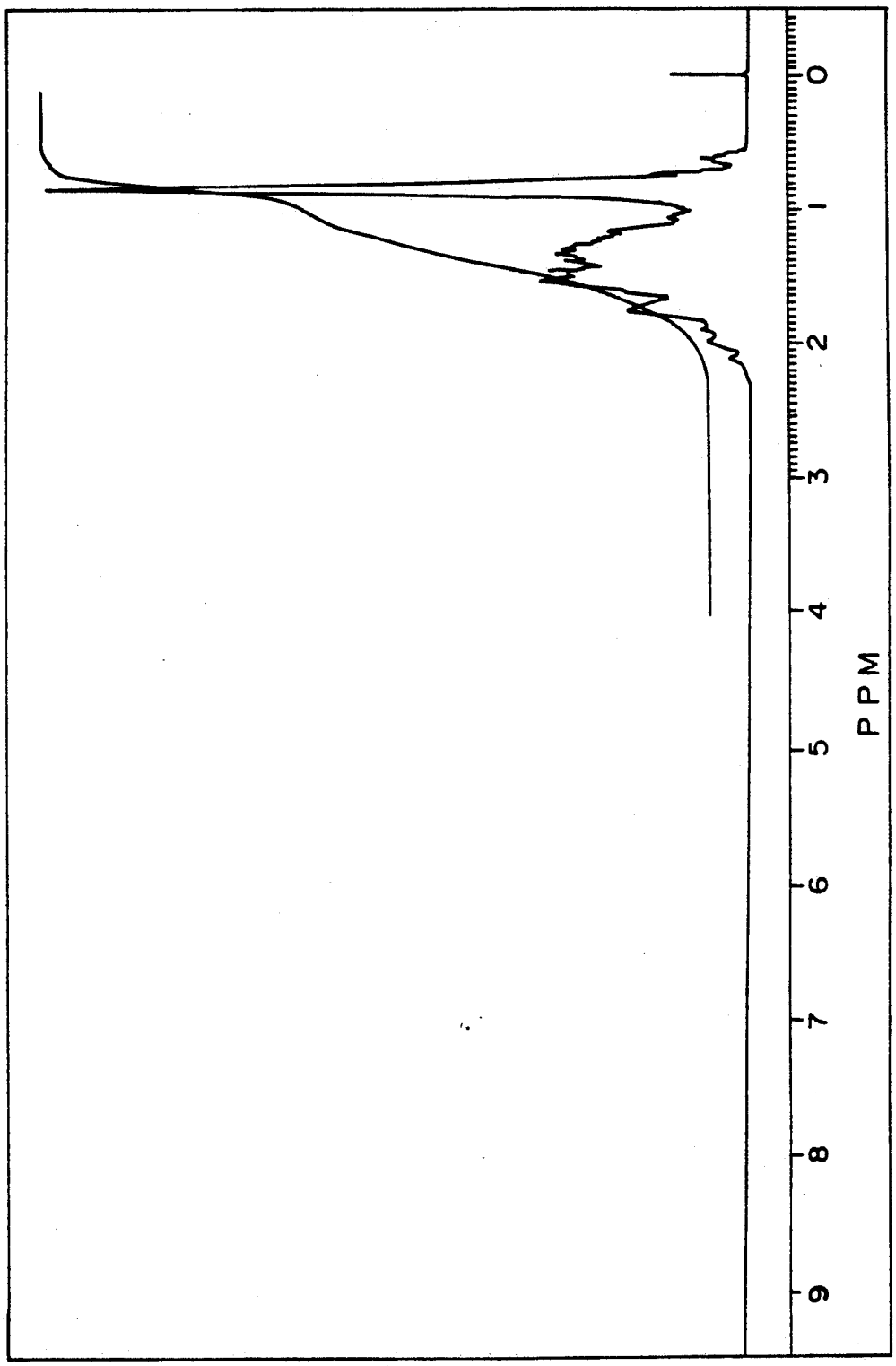
FIG. 4 is a $^1$H-NMR chart of the compound obtained in Example 1.
Figure 5:
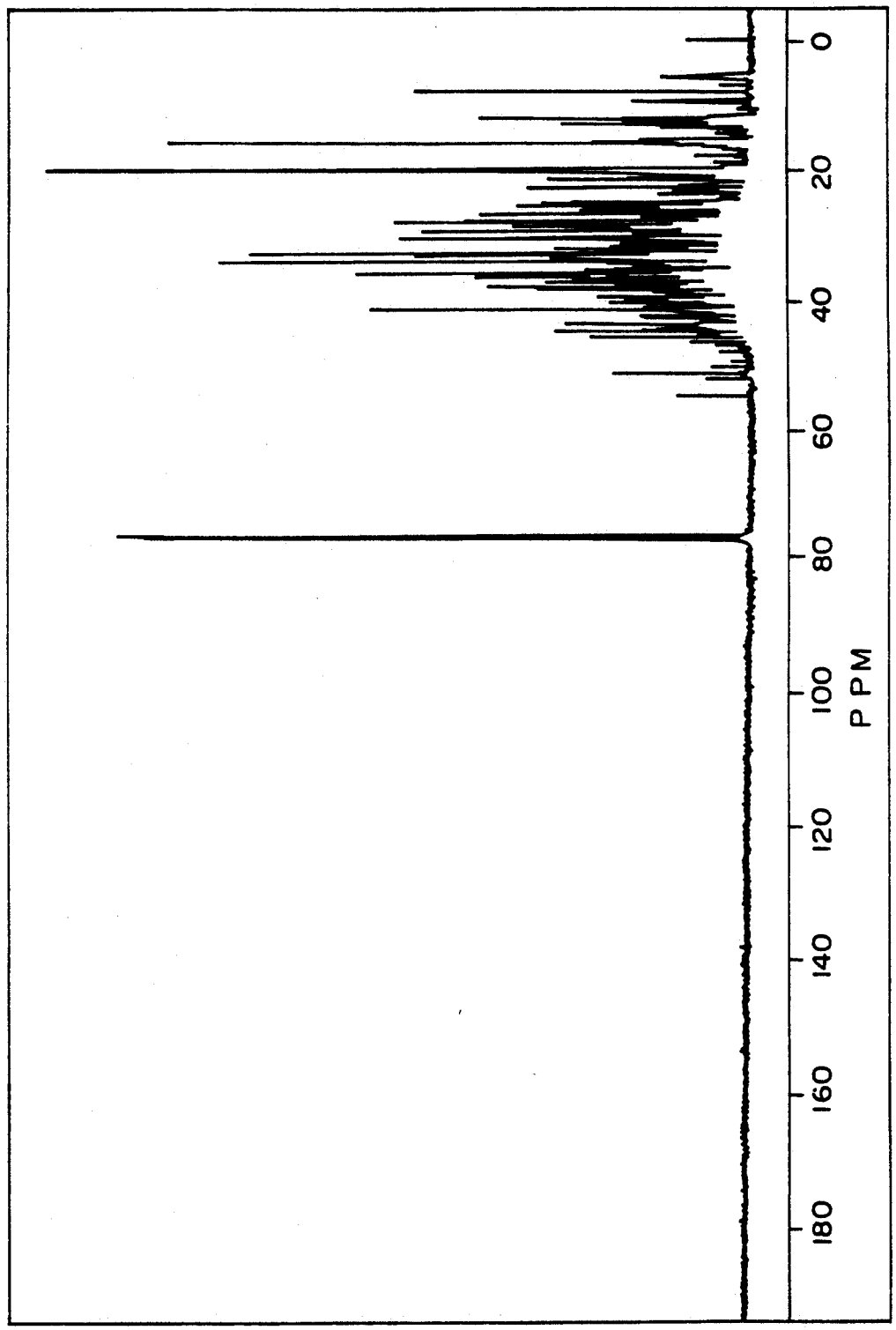
FIG. 5 is a $^{13}$C-NMR chart of the compound obtained in Example 1.
Figure 6:
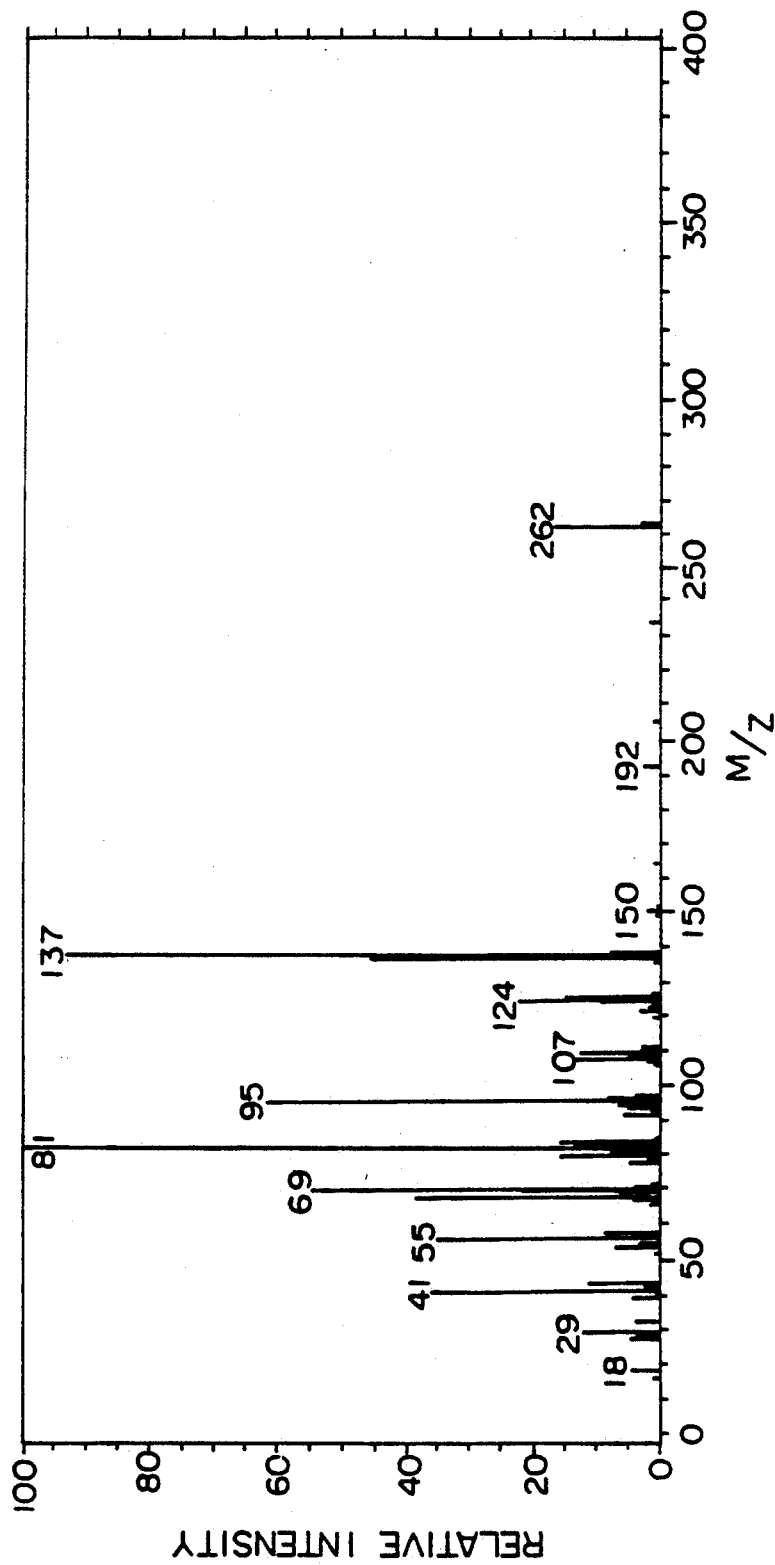
FIG. 6 is a MS chart of the compound obtained in Example 1.

The NMR analysis showed that the degree of hydrogenation was 99%. The so obtained reaction product was analyzed with NMR, IR and MS, resulting in a finding that it was 1-(2-bicyclo[2.2.2]octyl)-1-(trimethylcyclohexyl)-ethane. Further, the traction coefficient of the obtained reaction product was determined in a temperature range of 40° C. to 140° C. and the results are shown in FIG. 1. The graphs of $^1$H-NMR, $^{13}$C-NMR and MS of the reaction product are respectively shown in FIGS. 4 to 6.

The reaction product also was found to have the following properties:

| Kinematic viscosity | 35.86 cSt (40° C.) |
| --- | --- |
| | 4.289 cSt (100° C.) |
| Viscosity index | −99 |
| Specific gravity (15/4° C.) | 0.9329 |
| Pour point | −25.0° C. |
| Refractive index ($n^{20}_d$) | 1.4989 |

EXAMPLE 2

(1) The preparation of 2-hydroxymethylbicyclo[2.2.2]octane 755 cc of 2-hydroxymethylbicyclo[2.2.2]octane was obtained by carrying out the Diels-Alder reaction and then the hydrogenation in accordance with substantially the same procedure as in (1) of Example 1, except that methyl vinyl ketone used therein was replaced by 430 ml of acrolein.

(2) The preparation of 2-methylenebicyclo[2.2.2]octane and 2-methylbicyclo[2.2.2]-2-octene.

In a quartz glass, a normal pressure flow reactor having an outer diameter of 20 mm and a length of 500 mm, 15 g of γ-alumina (Norton Alumina SA-6273 brand supplied by Nikka Seikoh Co., Ltd.) was placed, then the compound obtained in (1) above was subjected to the dehydration a reaction under the conditions of reaction temperature of 320° C. and a weight hourly space velocity (WHSV) of 1.07 hr$^{-1}$ and 356 g of a dehydration product comprising 80% of 2-methylenebicyclo[2.2.2]octane and 20% of 2-methylbicyclo[2.2.2]-2-octene was obtained. The dehydration product was subjected to rectification and each fraction resulted therefrom was identified with a measurement by NMR and MS.

(3) The preparation of a hydrogenated dimer from the dehydration product obtained in (2) above 313 g of said dehydration mixture was placed in a 1 liter four neck flask, followed by equipping said flask with a Dimroth reflux condenser and a thermometer. Added thereto was 50 g of activated clay (Galleon Earth NS brand supplied by Mizusawa Kagaku Co., Ltd.) which had been dried at 150° C. for a day and night, and the so obtained mixture was stirred at 140° C. for 5 hours. Then, the mixture was cooled to 100° C., the catalyst was filtered off, the unreacted starting materials were distilled off and as the result 132 g of the reaction product was obtained.

Figure 7:
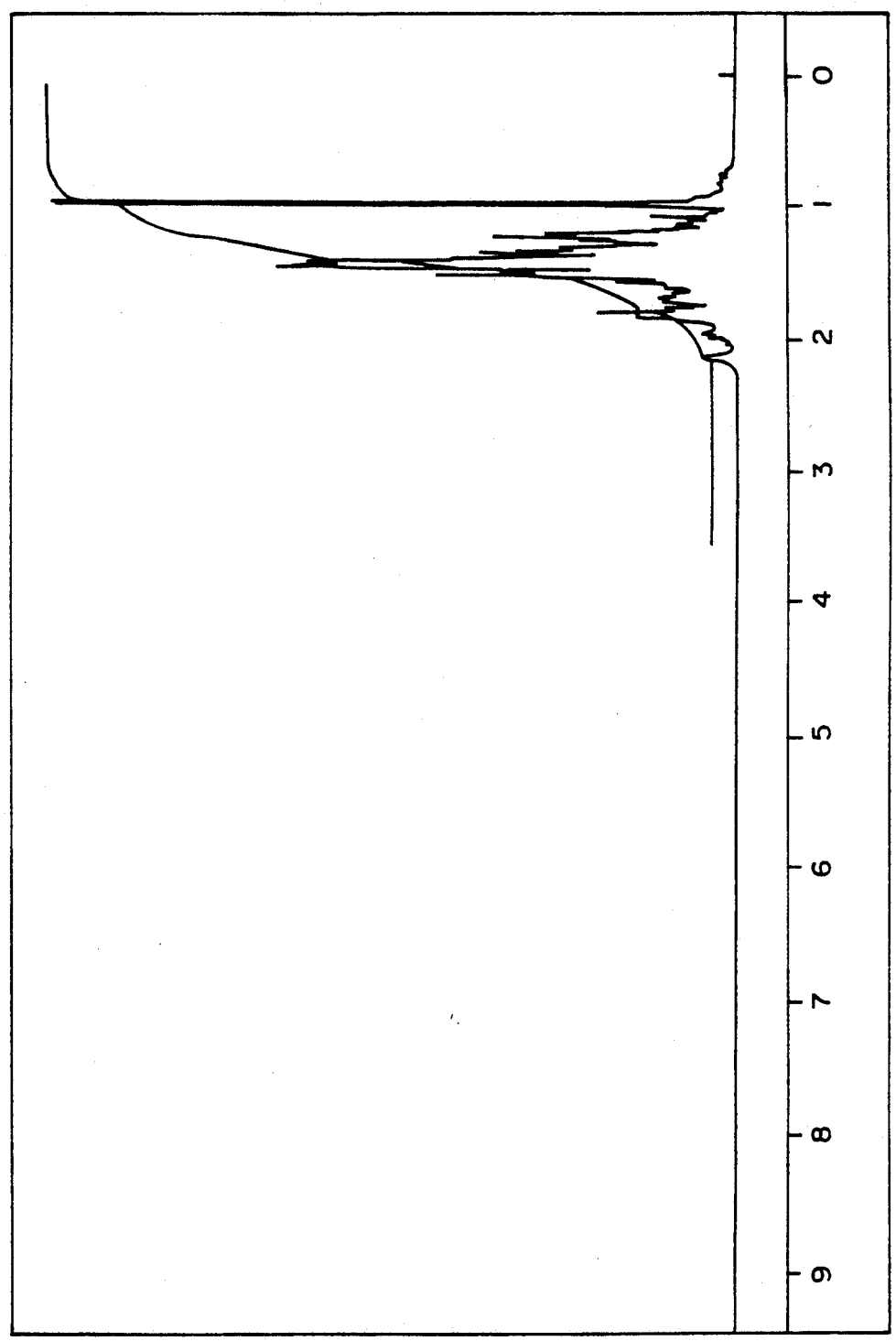
FIG. 7 is a $^1$H-NMR chart of the compound obtained in Example 2.
Figure 8:
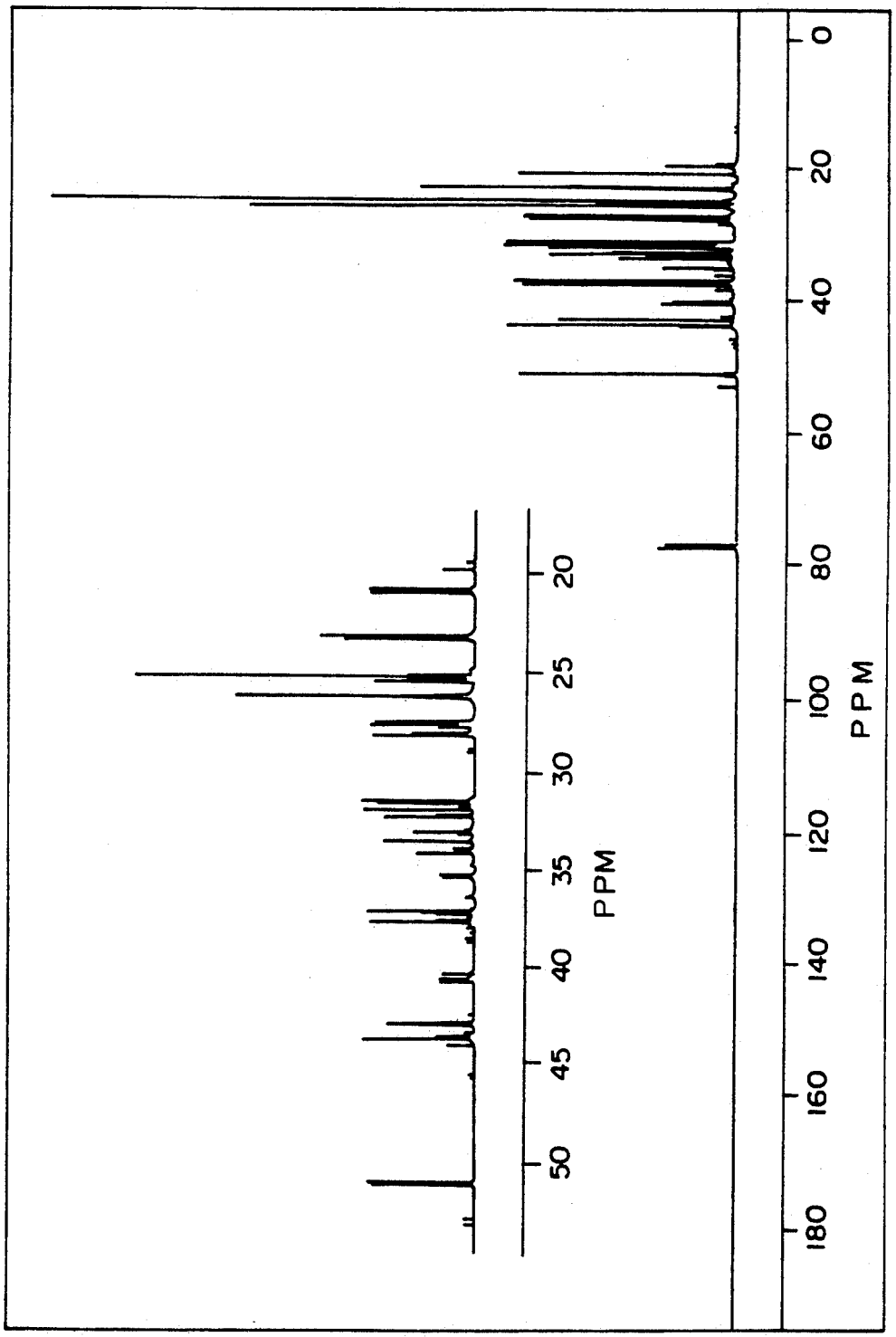
FIG. 8 is a $^{13}$C-NMR chart of the compound obtained in Example 2.
Figure 9:
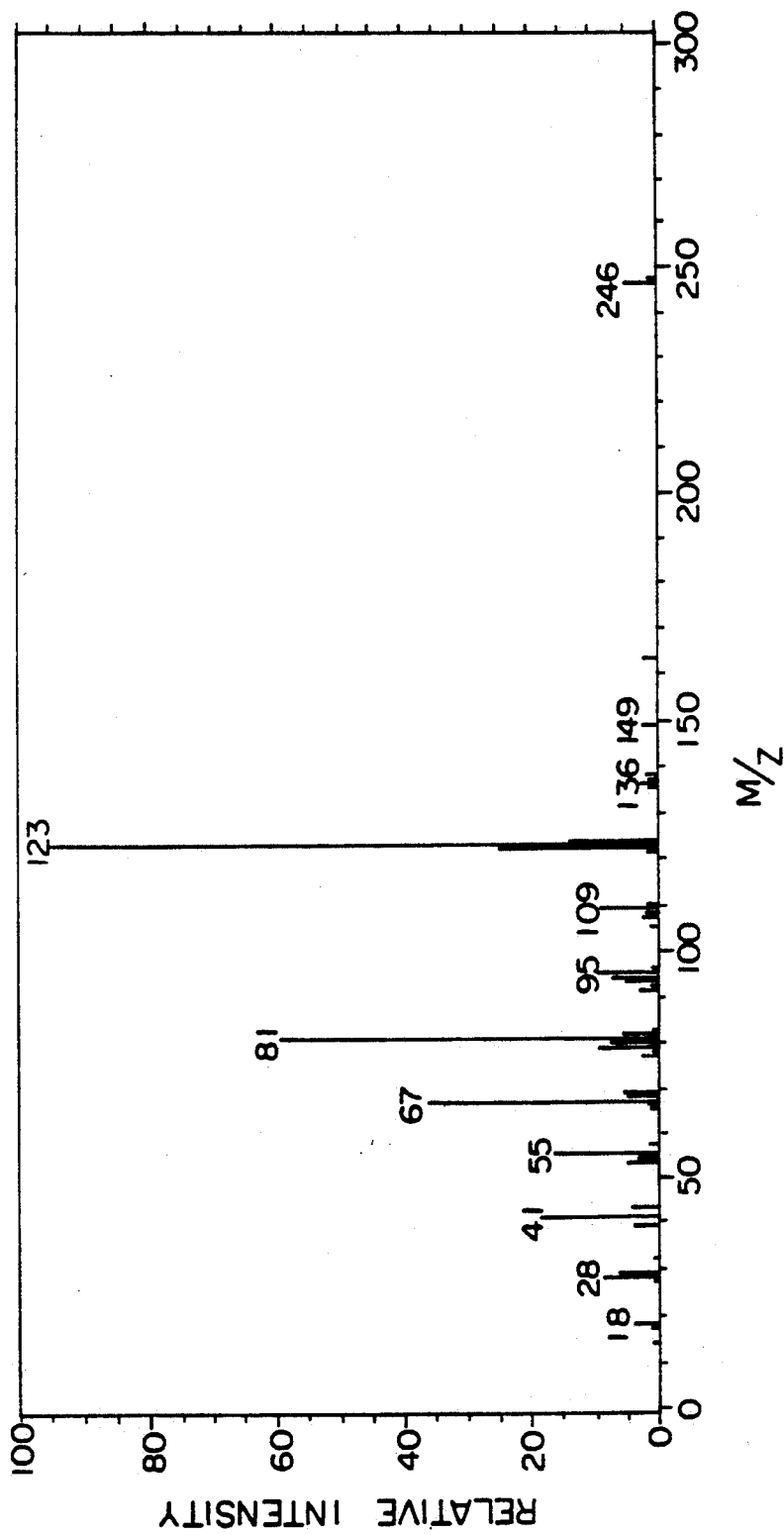
FIG. 9 is a MS chart of the compound obtained in Example 2.

The so obtained reaction product was placed in a 1 liter autoclave, 300 ml of methylcyclohexane as the solvent and 10 g of nickel/diatomaceous earth catalyst (N-113 brand supplied by Nikki Kagaku Co., Ltd.) were added and the resulting mixture was hydrogenated under the conditions of a hydrogen pressure of 70 kg/cm$^2$G, a reaction temperature of 200° C. and a reaction time of 3 hours. The mixture was cooled to room temperature, the catalyst was filtered off, the solvent was distilled off, the residue was distilled under reduced pressure and 116 g of a fraction having a boiling point of 148° to 154° C./2 mmHg was obtained. The analysis with NMR and MS showed that the so obtained reaction product was a hydrogenated dimer of above-mentioned olefin, that is, a compound having 2 bicyclo[2.2.2]octane rings per molecule to represent the complete hydrogenation and be formulated as 1-(2-methyl-bicyclo[2.2.2]-2-octyl)-1-(bicyclo[2.2.2]-2-octyl)methane with the composition formula of $C_{18}H_{30}$. This novel compound was analyzed with $^1$H-NMR, $^{13}$C-NMR and MS and the graphs of these measurements are respectively shown in FIGS. 7 to 9. The traction coefficient of this novel compound was measured as well and the result is shown in FIG. 1.

The reaction product obtained above was found to have the following properties:

| Kinematic viscosity | 78.55 cSt (40° C.) |
| --- | --- |
| | 7.465 cSt (100° C.) |
| Viscosity index | 28 |
| Specific gravity (15/4° C.) | 0.9908 |
| Pour point | −27.5° C. |
| Refractive index ($n^{20}_d$) | 1.5205 |

EXAMPLE 3

(1) The preparation of 2-hydroxymethyl-3-methylbicyclo[2.2.1]heptane

In a 1 liter autoclave, 351 g of crotonaldehyde and 250 g of dicyclopentadiene were placed and allowed to react at 170° C. for 3 hours. After cooling, 20 g of 5% ruthenium/carbon catalyst (supplied by N. E. Chemcat Corp.) was added thereto and the resulting mixture was hydrogenated under the conditions of a hydrogen pressure of 70 kg/cm$^2$G, a reaction temperature of 180° C. and a reaction time of 4 hours. The so processed mixture was cooled, the catalyst was filtered off, the filtrate was distilled off under reduced pressure and 270 g of a fraction having a boiling point of 70° C./0.9 mmHg was obtained. The analysis with NMR, IR and MS showed that the obtained product was 2-hydroxymethyl-3-methylbicyclo[2.2.1]heptane.

The above-mentioned procedure was repeated to obtain two batches of said reaction product totaling 820 g.

(2) The preparation of 4-methyl-bicyclo[3.2.1]-2-octene by dehydrating and isomerizing the compound obtained in (1) above A 500 ml four neck flask was equipped with a thermometer, a stirrer and a Dean-Stark type dehydrator, and 200 ml of hydrogenated paraffinic mineral oil (150 neutral oil) as the solvent and 20 g of heteropolyacid (phosphotungstic acid) as the catalyst were placed therein. With stirring at 180° C., 2-hydroxymethyl-3-methylbicyclo[2.2.1]heptane obtained in (1) above was dropped therein at a rate of one drop per 2 seconds using a dropping funnel. As the result, 2-hydroxymethyl-3-methylbicyclo[2.2.1]heptane underwent the immediate dehydration reaction, distilling off olefin along with water. When said olefin distillate totaled 500 g, the reaction was stopped, and the olefin distillate was distilled again by means of rectification under atmospheric pressure and 370 g of a fraction having a boiling point of 135° to 138° C. was obtained. The analysis with NMR and MS showed that the obtained reaction product (the dehydration product from 2-hydroxymethyl-3-methylbicyclo[2.2.1]heptane) has a bicyclo[3.2.1]octane skeleton and a bicyclo[3.3.0]octane skeleton both of which had resulted from the isomerization of the bicyclo[2.2.1]heptane skeleton.

(3) The preparation of a hydrogenated dimer from the dehydration product of 2-hydroxymethyl-3-methyl-bicyclo[2.2.1]heptane A 1 liter four neck flask was equipped with a thermometer, a stirrer and a Dimroth reflux condenser, and 300 ml of n-hexane as the solvent and 10 ml of $BF_3.1.5$ $H_2O$ complex as the catalyst were placed therein. Then, 300 g of the reaction product obtained in (2) above was gently dropped therein with stirring. There was a slight exothermic reaction during this process. After dropping, the mixture was stirred at 30° C. for 1 hour, the temperature was elevated to 55° C. to continue stirring for another 1 hour and then the content of the flask was poured into 500 ml of water to stop the reaction.

An organic layer produced therein was washed twice with 200 ml of 2N NaOH aqueous solution, then again washed twice with 200 ml of water and dried with anhydrous $MgSO_4$. Then, the so processed organic layer was distilled under reduced pressure and 150 g of a fraction having a boiling point of 135° to 142° C./2 mmHg was obtained.

Figure 2:
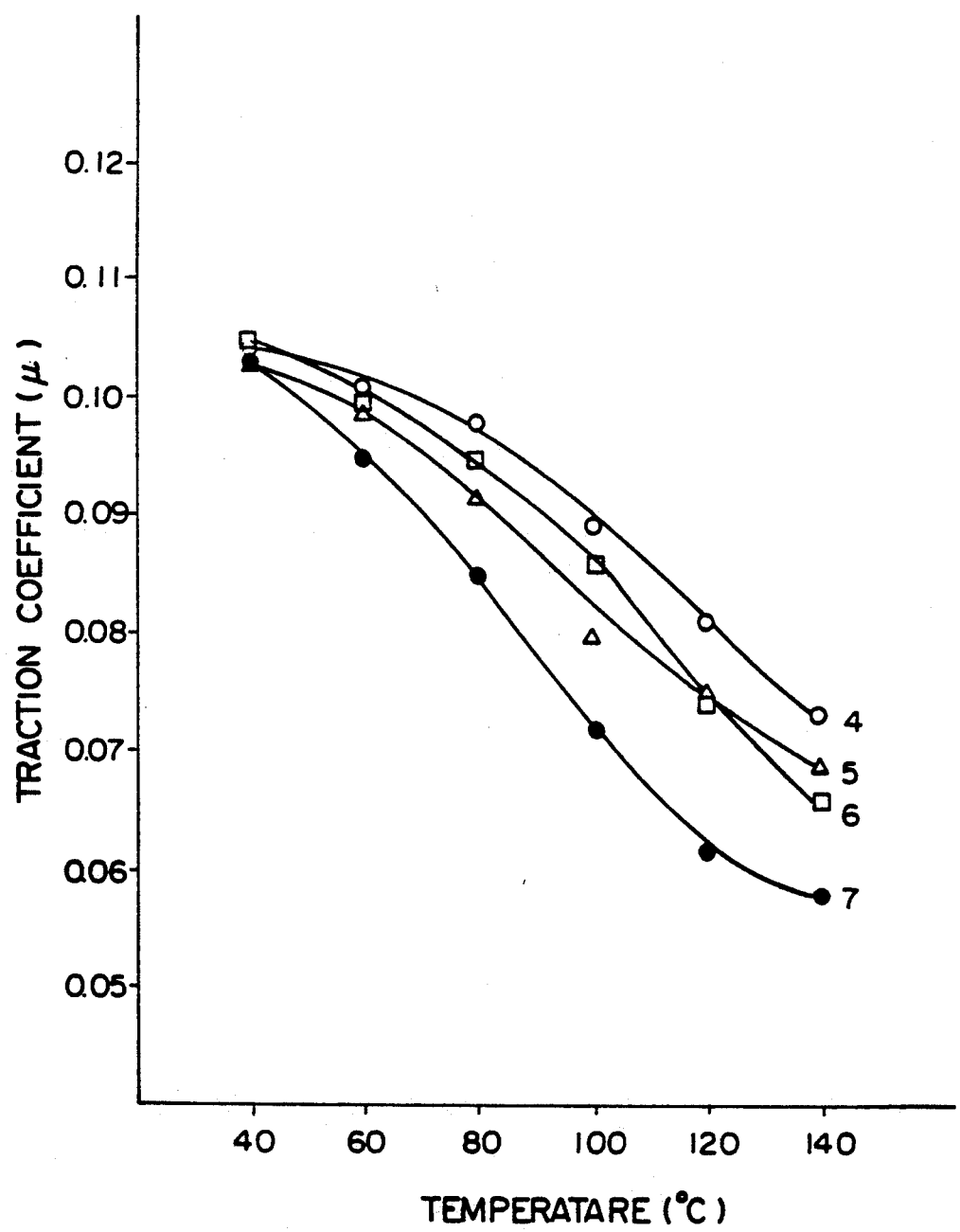
FIG. 2 is a graph showing temperature dependence of the traction coefficient in connection with the compounds of Example 3, Example 4, Example 7 and Comparative Example 2.
Figure 10:
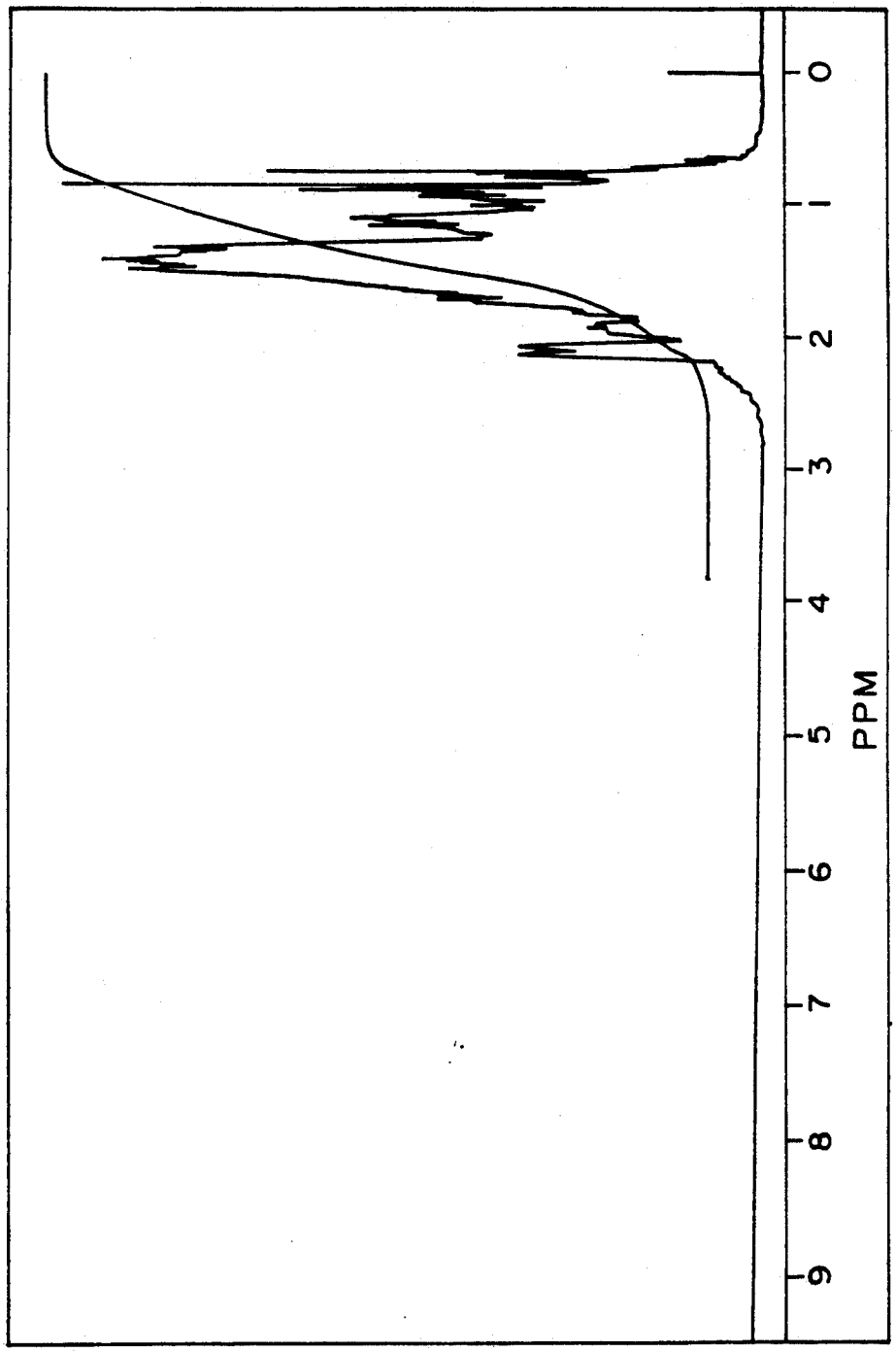
FIG. 10 is a $^1$H-NMR chart of the compound obtained in Example 3.
Figure 11:
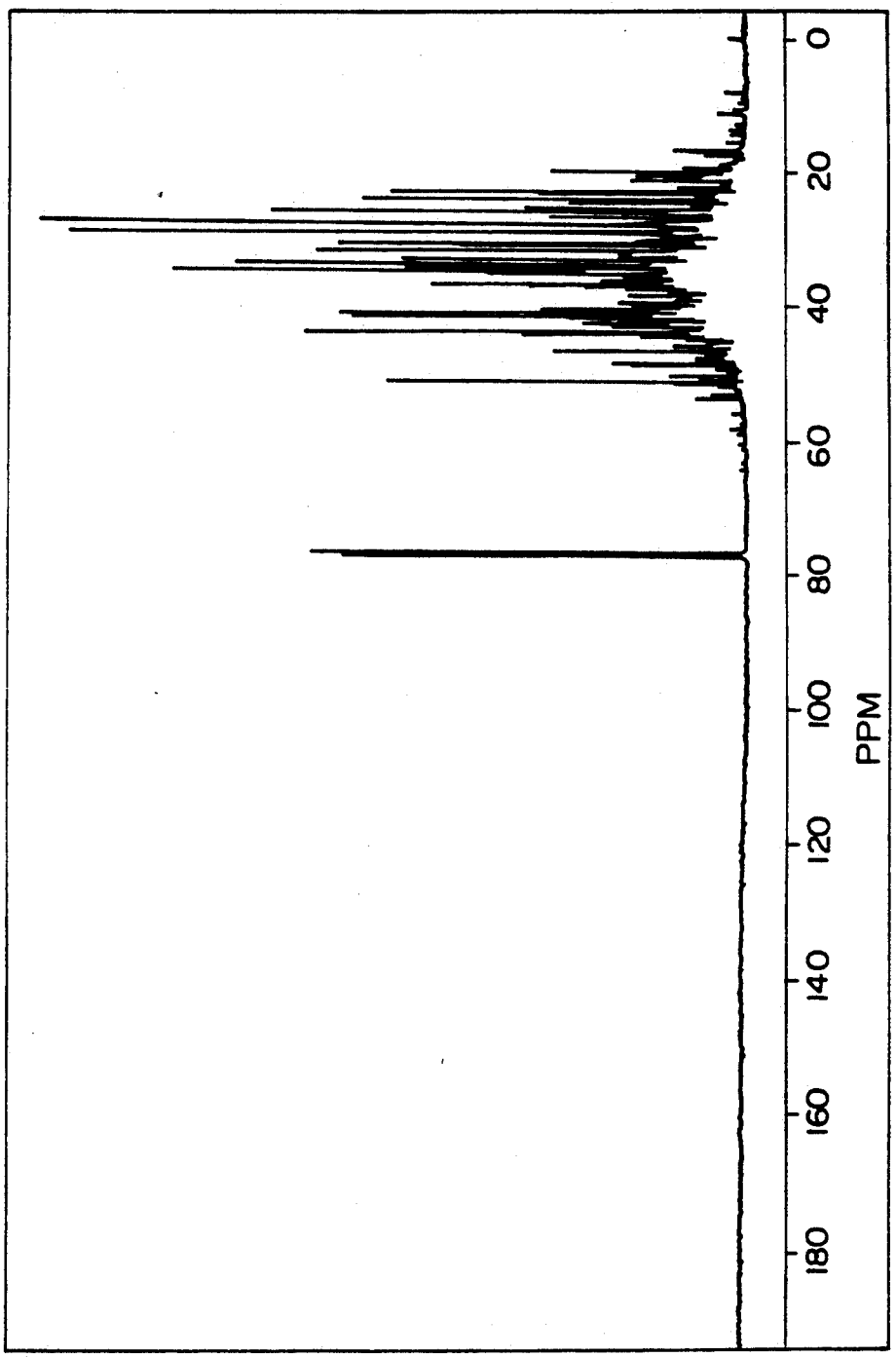
FIG. 11 is a $^{13}$C-NMR chart of the compound obtained in Example 3.
Figure 12:
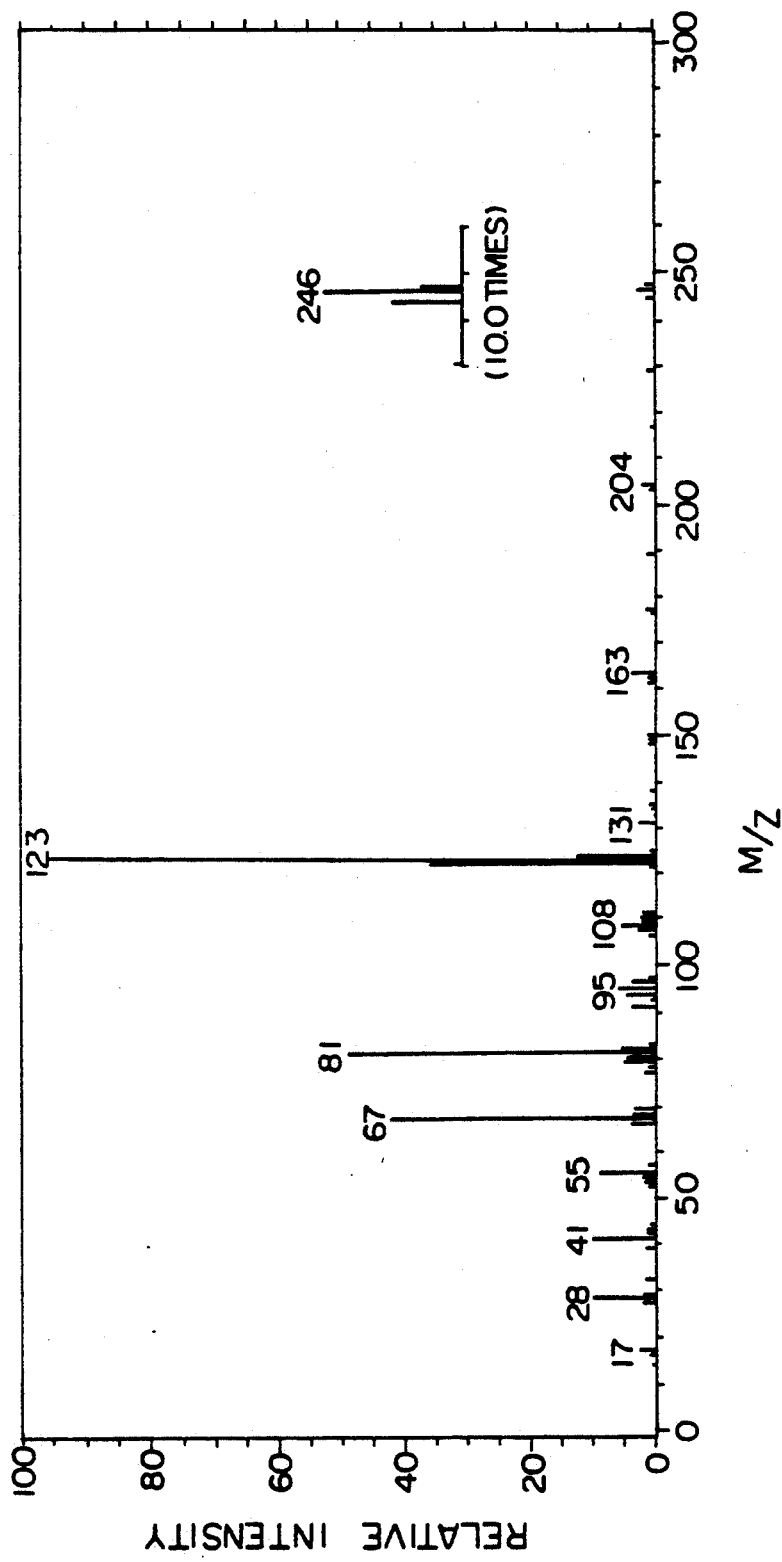
FIG. 12 is a MS chart of the compound obtained in Example 3.

Said fraction was placed in a 1 liter autoclave and hydrogenated in substantially the same procedure as in Example 2. The resulting product was analyzed, and the results showed that the degree of hydrogenation of said product was 99% and that it was hydrocarbon having a bicyclo[3.2.1]octane skeleton and/or a bicyclo[3.3.0]octane skeleton per molecule (Composition formula: $C_{18}H_{30}$). This novel compound was analyzed with $^1$H-NMR, $^{13}$C-NMR and MS and the graphs of these measurements are respectively shown in FIGS. 10 to 12. The traction coefficient of this compound also was measured and the results are shown in FIG. 2.

Further, the compound was found to have the following properties:

| Kinematic viscosity | 36.74 cSt (40° C.) |
| | 5.331 cSt (100° C.) |
| Viscosity index | 65 |
| Specific gravity (15/4° C.) | 0.9868 |
| Pour point | −40.0 |
| Refractive index ($n^{20}_d$) | 1.5191 |

EXAMPLE 4

The single batch synthesis of a dehydration isomerized dimer of the compound obtained in Example 3 above.

A 1 liter four neck flask was equipped with a thermometer, a stirrer and a Dean-Stark type dehydrator, and 510 g of 2-hydroxymethyl-3-methylbicyclo[2.2.1]heptane obtained in Example 3 above and 25 g of phosphotungstic acid were placed therein. The resulting mixture was stirred at a reaction temperature of 150° C. and water was evolved as a result of dehydration reaction. Said water alone was distilled off in a gentle stream of argon gas and the residue was stirred for 4 hours. Said residue was cooled to room temperature, the catalyst was filtered off and the content of the flask was analyzed, with a resulting GC pattern which was different from that of Example 3. Then, a fraction having a boiling point of 130° to 138° C./2 mmHg was obtained by distillation, and the analysis with NMR and MS showed that the obtained fraction was an isomerized dimer as the compound of Example 3 was and a position isomer of said compound.

The so obtained reaction product was hydrogenated in accordance with substantially the same procedure as in Example 3 and the analysis of the end product resulted in a finding that the degree of hydrogenation was 99%. The traction coefficient of this hydrogenation product was measured and the results are shown in FIG. 2.

Said hydrogenation product also was found to have the following properties:

| Kinematic viscosity | 30.18 cSt (40° C.) |
| | 4.448 cSt (100° C.) |
| Viscosity index | 13 |
| Specific gravity (15/4° C.) | 0.9722 |
| Pour point | −42.5° C. |
| Refractive index ($n^{20}_d$) | 1.5076 |

EXAMPLE 5

(1) The preparation of 2-methylene-3-methyl-bicyclo[2.2.1]heptane and 2,3-dimethyl-bicyclo[2.2.1]-2-heptene 2-hydroxymethyl-3-methylbicyclo[2.2.1]heptane obtained in (1) of Example 3 was caused to react in the flow dehydration reactor used in (2) of Example 2 and the dehydration product was obtained in accordance with substantially the same procedure as therein. The analysis with NMR, MS and GC resulted in a finding that it was a mixture of 60% of 2-methylene-3-methyl-bicyclo[2.2.1]heptane and 40% of 2,3-dimethyl-bicyclo[2.2.1]-2-heptene, each component having no isomerized structure.

(2) The preparation of a hydrogenated co-dimer comprising the dehydration product obtained in (1) above and that of (2) of Example 3.

In a 5 liter four neck flask, 1.5 liter of the olefin mixture (of 2-methylene-3-methyl-bicyclo[2.2.1]heptane and 2,3-dimethyl-bicyclo[2.2.1]-2-heptene) as described in (1) above and 1.5 liter of the dehydration product obtained in (2) of Example 3 were placed and 250 g of activated clay which had been dried at 150° C. for a day and night were added thereto.

The so obtained mixture was maintained at a reaction temperature of 180° C. with stirring for 7 hours and then cooled down to 100° C., the catalyst was filtered off and the unreacted starting materials were recovered. The analysis of the residual solution showed that there were roughly 2 major patterns in the GC finding. However, the dimers of bicyclo[3.2.1]octenes and/or bicyclo[3.3.0]octenes were not observed as they were in Examples 3 and 4. Said residual solution was distilled under reduced pressure to obtain 200 g of a fraction having a boiling point of 112° to 125° C./2 mmHg and 976 g of a fraction having a boiling point of 128° to 137° C./2 mmHg. The analysis with NMR and MS resulted in a finding that the former fraction was a dimer of bicyclo[2.2.1]heptanes and that the latter major fraction had one each of bicyclo[2.2.1]heptane skeleton and bicyclo[3.2.1]octane or bicyclo[3.3.0]octane skeleton per molecule. Therefore, the major fraction was found to be a co-dimer of $C_{18}H_{30}$.

Figure 13:
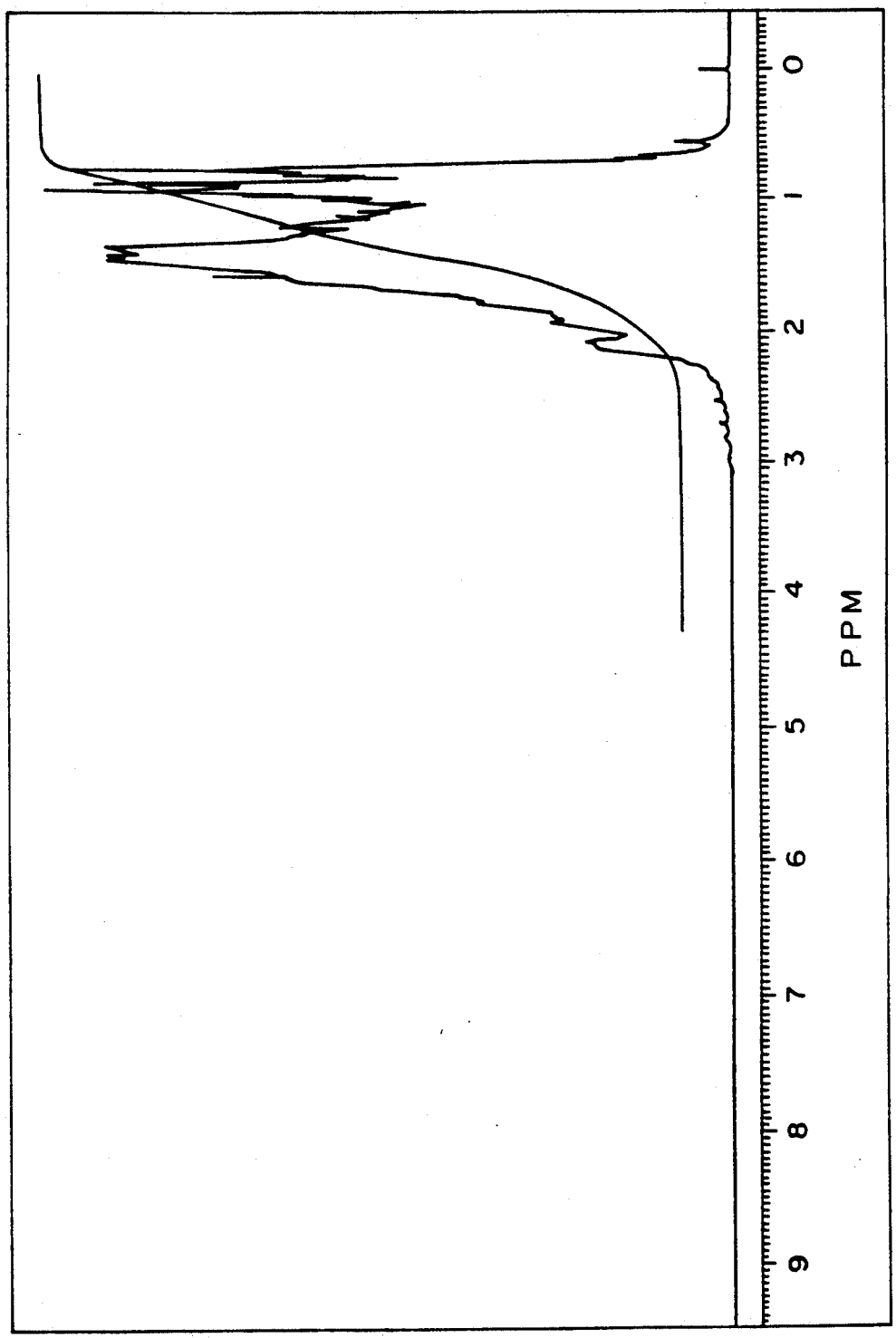
FIG. 13 is a $^1$H-NMR chart of the compound obtained in Example 5.
Figure 14:
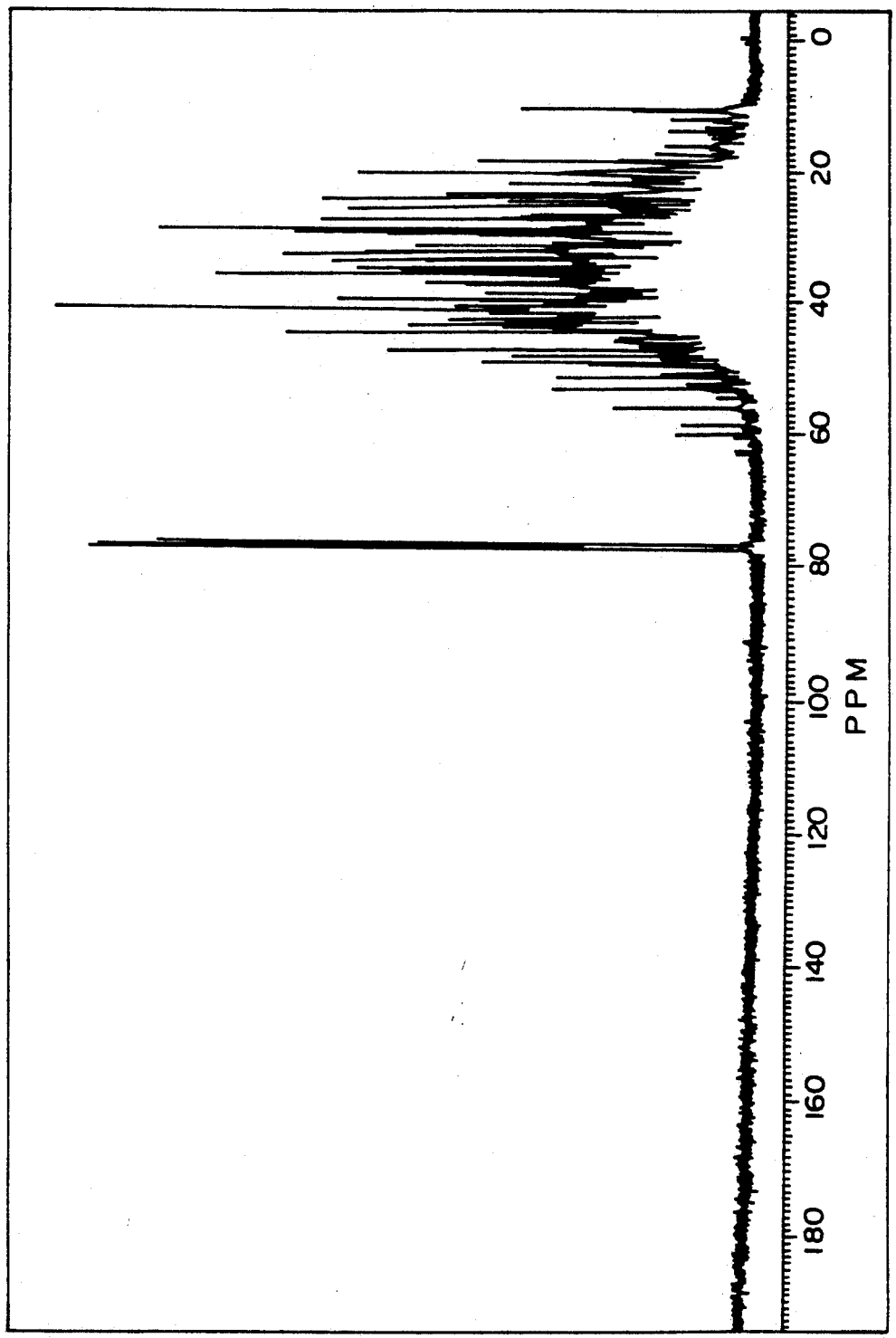
FIG. 14 is a $^{13}$C-NMR chart of the compound obtained in Example 5.
Figure 15:
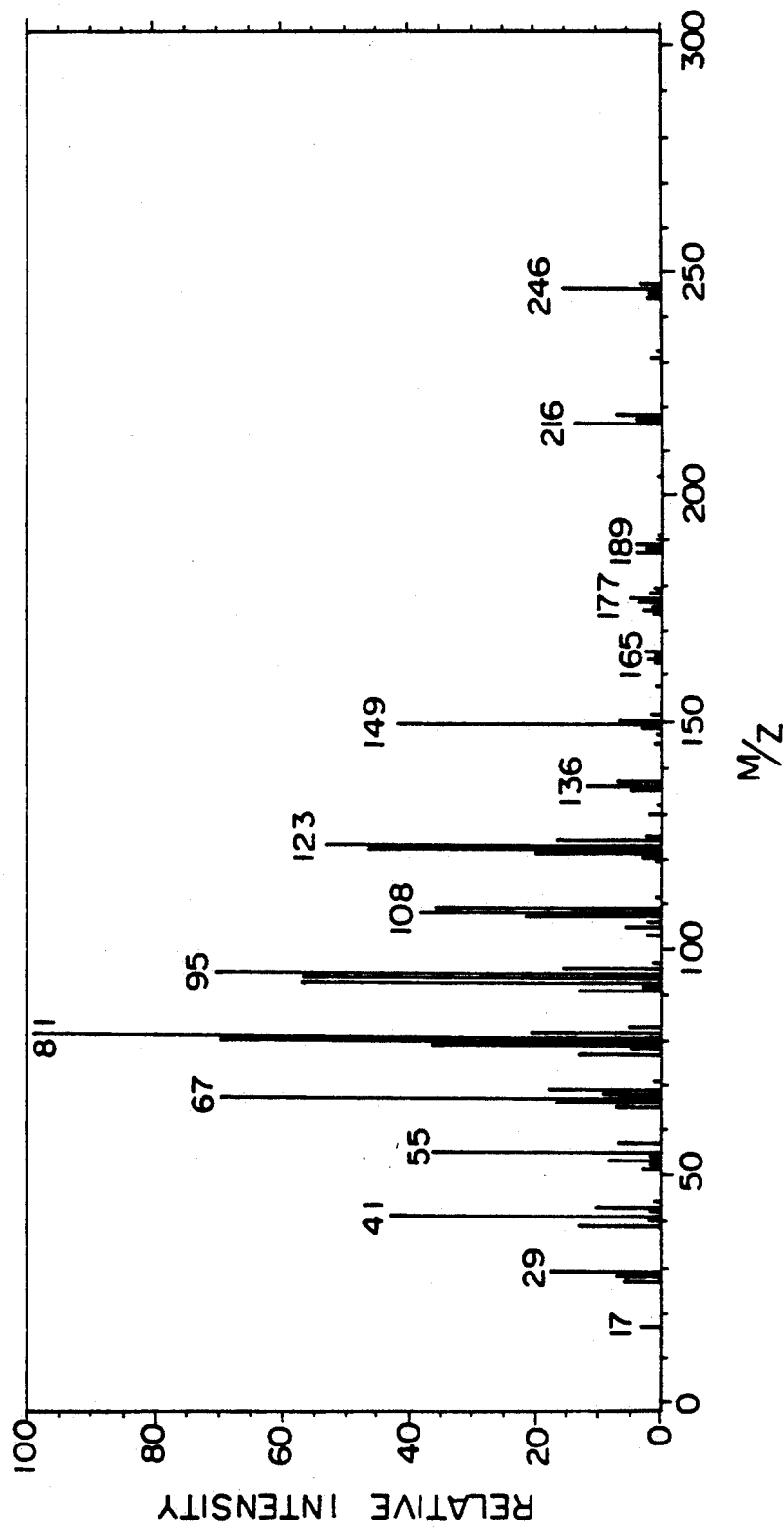
FIG. 15 is a MS chart of the compound obtained in Example 5.

The so obtained reaction product was hydrogenated in accordance with substantially the same procedure as in (3) of Example 3, with the result that the degree of hydrogenation was 99%. This novel compound was analyzed with $^1$H-NMR, $^{13}$C-NMR and MS and the graphs of these measurements are respectively shown in FIGS. 13 to 15. The traction coefficient of the compound was measured and the results are sown in FIG. 3.

Further, the reaction product obtained as above was found to have the following properties:

| Kinematic viscosity | 26.18 cSt (40° C.) |
|---|---|
|  | 4.281 cSt (100° C.) |
| Viscosity index | 38 |
| Specific gravity (15/4° C.) | 0.9739 |
| Pour point | −37.5° C. |
| Refractive index ($n^{20}_d$) | 1.5121 |

EXAMPLE 6

(1) The preparation of 2-hydroxymethyl-bicyclo[2.2.1]heptane 760 g of 2-hydroxymethyl-bicyclo[2.2.1]heptane was obtained by carrying out the Deals-Alder reaction and then the hydrogenation in accordance with substantially the same procedure as in (1) of Example 3, except that crotonaldehyde used therein was replaced by acrolein.

(2) The preparation of bicyclo[3.2.1]-2-octene by dehydrating and isomerizing the compound obtained in (1) above The dehydration isomerization reaction was conducted in accordance with substantially the same procedure as in (2) of Example 3, except that 2-hydroxymethyl-3-methylbicyclo[2.2.1]heptane was replaced by 2-hydroxymethyl-bicyclo[2.2.1]heptane obtained in (1) above and that the reaction temperature was changed to 170° C. As the result, 600 g of olefin having a GC purity of 98% was fractionated. The analysis with NMR and MS showed that the obtained reaction product was isomerized bicyclo[3.2.1]-2-octene. (3) The preparation of a hydrogenated co-dimer of bicyclo[3.2.1]-2-octene and dihydrodicyclopentadiene In a 1 liter autoclave, 396 g of dicyclopentadiene and 6 g of developed Raney cobalt catalyst were placed and hydrogenated under the conditions of hydrogen pressure of 15 kg/cm$^2$G and reaction temperature of 40° C. until 3 mol of hydrogen was absorbed. Then, the so processed mixture was cooled, the catalyst was filtered off and the analysis with NMR, MS and GC resulted in a finding that half as much as the starting material was converted into hydrogenated dihydrodicyclopentadiene having a GC purity of 98%.

Figure 3:
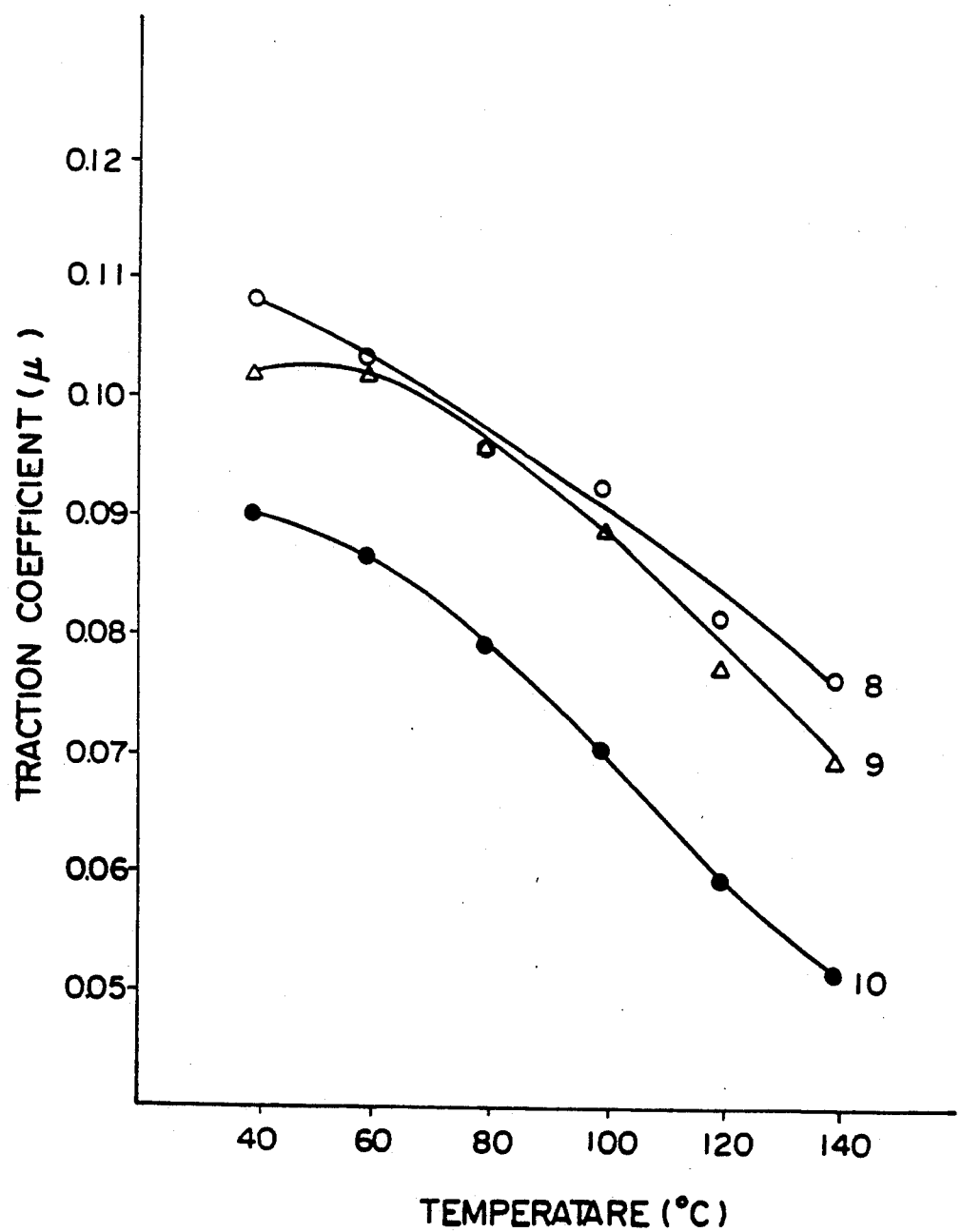
FIG. 3 is a graph showing temperature dependence of the traction coefficient in connection with the compounds of Example 5, Example 6 and Comparative Example 3.
Figure 16:
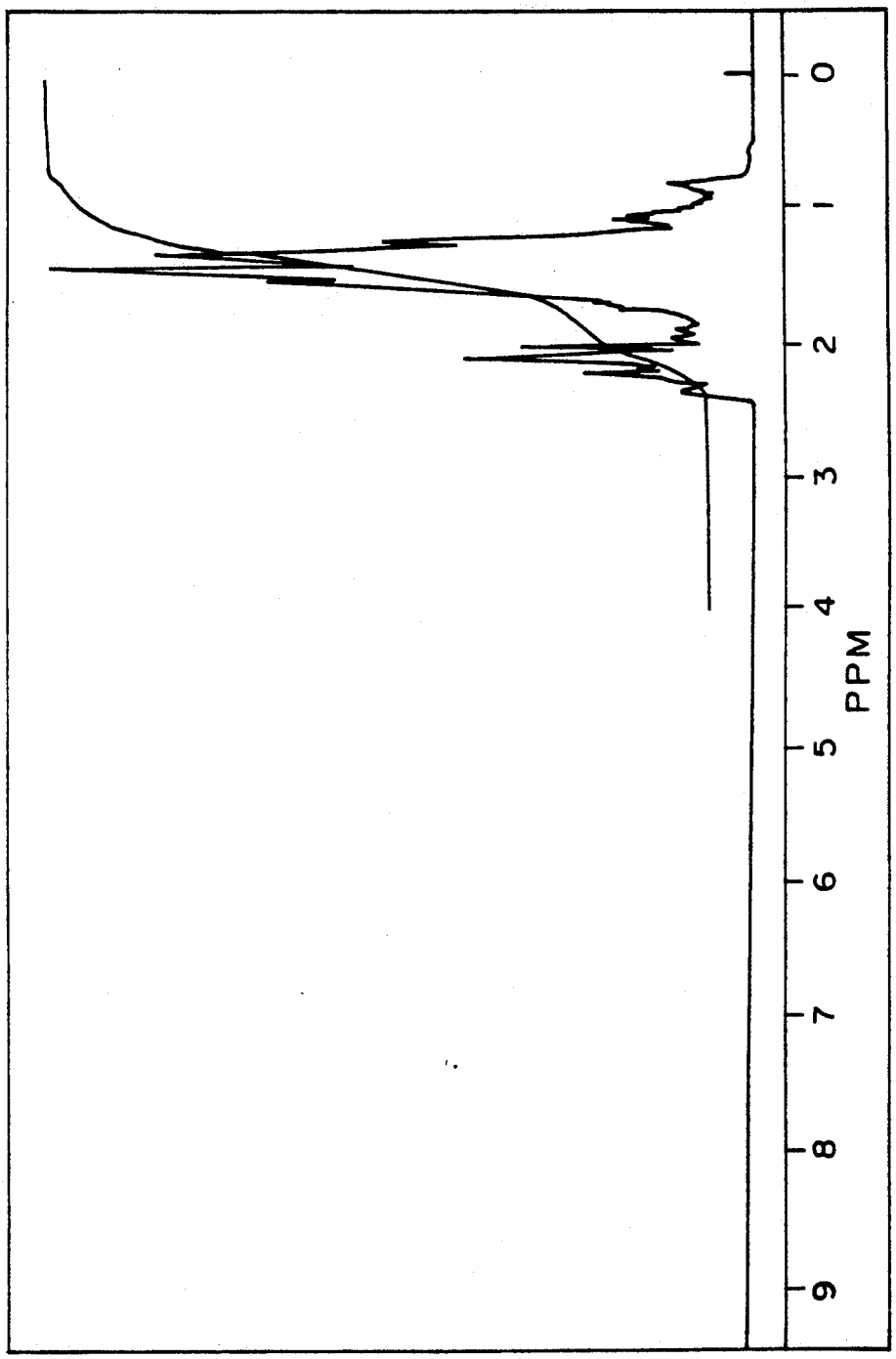
FIG. 16 is a $^1$H-NMR chart of the compound obtained in Example 6.
Figure 17:
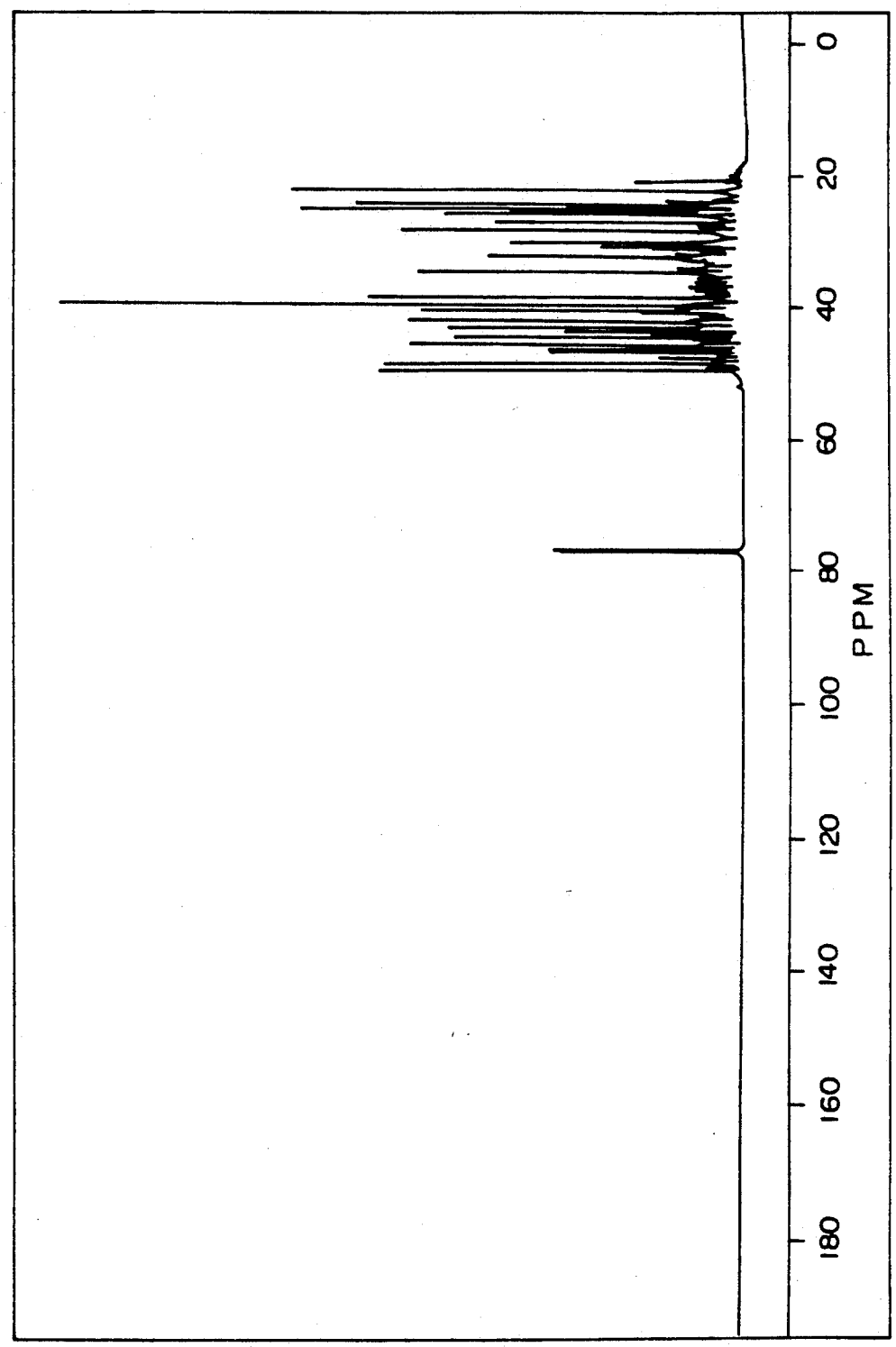
FIG. 17 is a $^{13}$C-NMR chart of the compound obtained in Example 6.
Figure 18:
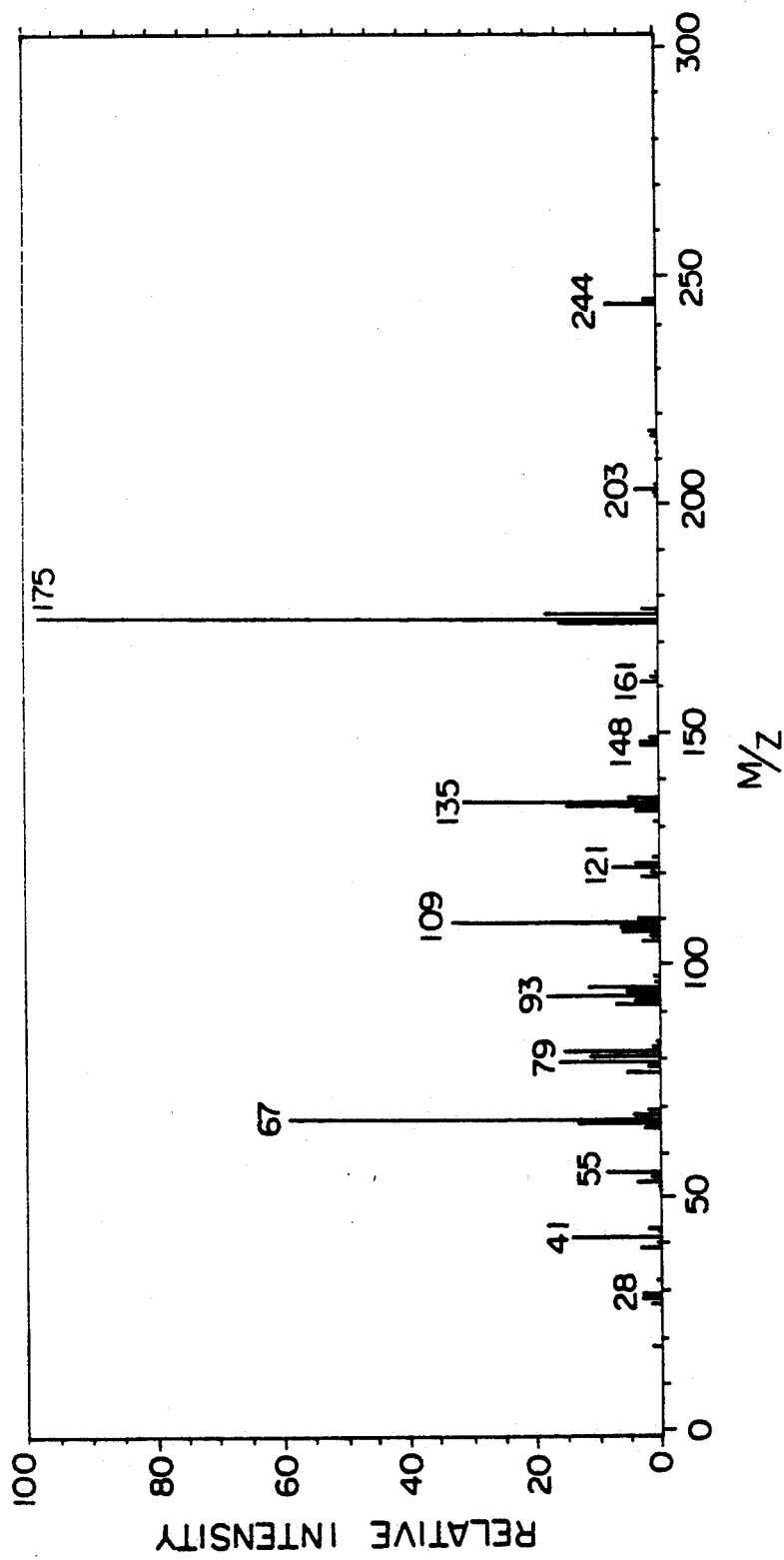
FIG. 18 is a MS chart of the compound obtained in Example 6.

Next, dihydrodicyclopentadiene and bicyclo[3.2.1]-2-octene obtained in (2) above were subjected to the co-dimerization reaction. The reaction was conducted by using BF$_3$.1.5H$_2$O complex catalyst and then carrying out the hydrogenation in accordance with substantially the same procedure as in the co-dimerization reaction in (3) of Example 3, except that 300 g of 4-methylbicyclo[3.2.1]-2-octene used therein was replaced by a mixture of 110 g of dihydrodicyclopentadiene and 240 g of bicyclo[3.2.1]-2-octene, and then 120 g of a fraction having a boiling point of 120° to 138° C./2 mmHg was obtained by distillation under reduced pressure. The analysis with NMR, MS and GC showed that said fraction was a mixture of 24% of C$_{18}$H$_{28}$ having one each of bicyclo[3.2.1]octane skeleton and tricyclo[5.2.1.0$^{2.6}$]-decane skeleton per molecule and 76% of the compound having 2 bicyclo[3.2.1]octane skeletons per molecule (composition formula: C$_{16}$H$_{26}$) as obtained in Example 7. This novel compound (the compound having one each of bicyclo[3.2.1]octane skeleton and tricyclo[5.2.1.0$^{2.6}$]decane skeleton per molecule) was fractionated by the liquid chromatography (LC), and with respect thereto the graphs of $^1$H-NMR, $^{13}$C-NMR and MS are respectively shown in FIGS. 16 to 18. The traction coefficient of this compound was measured and the results are shown in FIG. 3.

Further, the reaction product as obtained above was found to have the following properties:

| Kinematic viscosity | 33.91 cSt (40° C.) |
|---|---|
|  | 4.996 cSt (100° C.) |
| Viscosity index | 54 |
| Specific gravity (15/4° C.) | 1.0060 |
| Pour point | −42.5° C. |
| Refractive index ($n^{20}_d$) | 1.5259 |

EXAMPLE 7

The preparation of a dehydration isomerized dimer of 2-hydroxymethyl-bicyclo[2.2.1]heptane 500 g of 2-hydroxymethyl-bicyclo[2,2,1]heptane obtained in (1) of Example 6 was dimerized on a single batch basis by carrying out the dehydration and isomerization reaction in accordance with substantially the same procedure as in Example 4.

250 g of a fraction having a boiling point of 116° to 122° C./2 mmHg was obtained by distillation under reduced pressure. The fraction was analyzed with NMR, MS and GC, resulting in a finding that it was a compound having 2 bicyclo[3.2.1]octane skeletons per molecule (Composition formula: C$_{16}$H$_{26}$). The compound was hydrogenated in accordance with substantially the same procedure as in Example 4, with result that the degree of hydrogenation was 99%.

Figure 19:
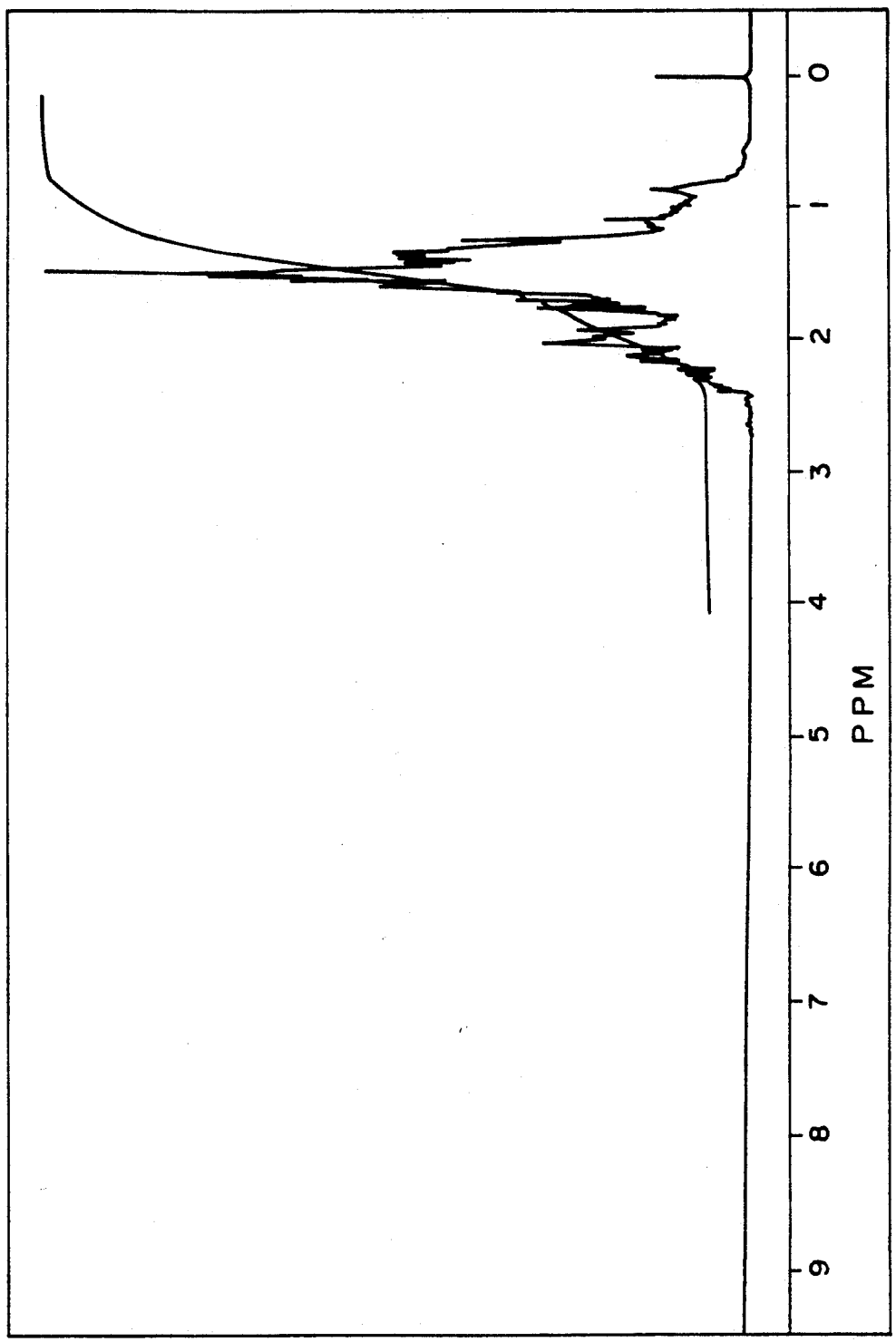
FIG. 19 is a $^1$H-NMR chart of the compound obtained in Example 7.
Figure 20:
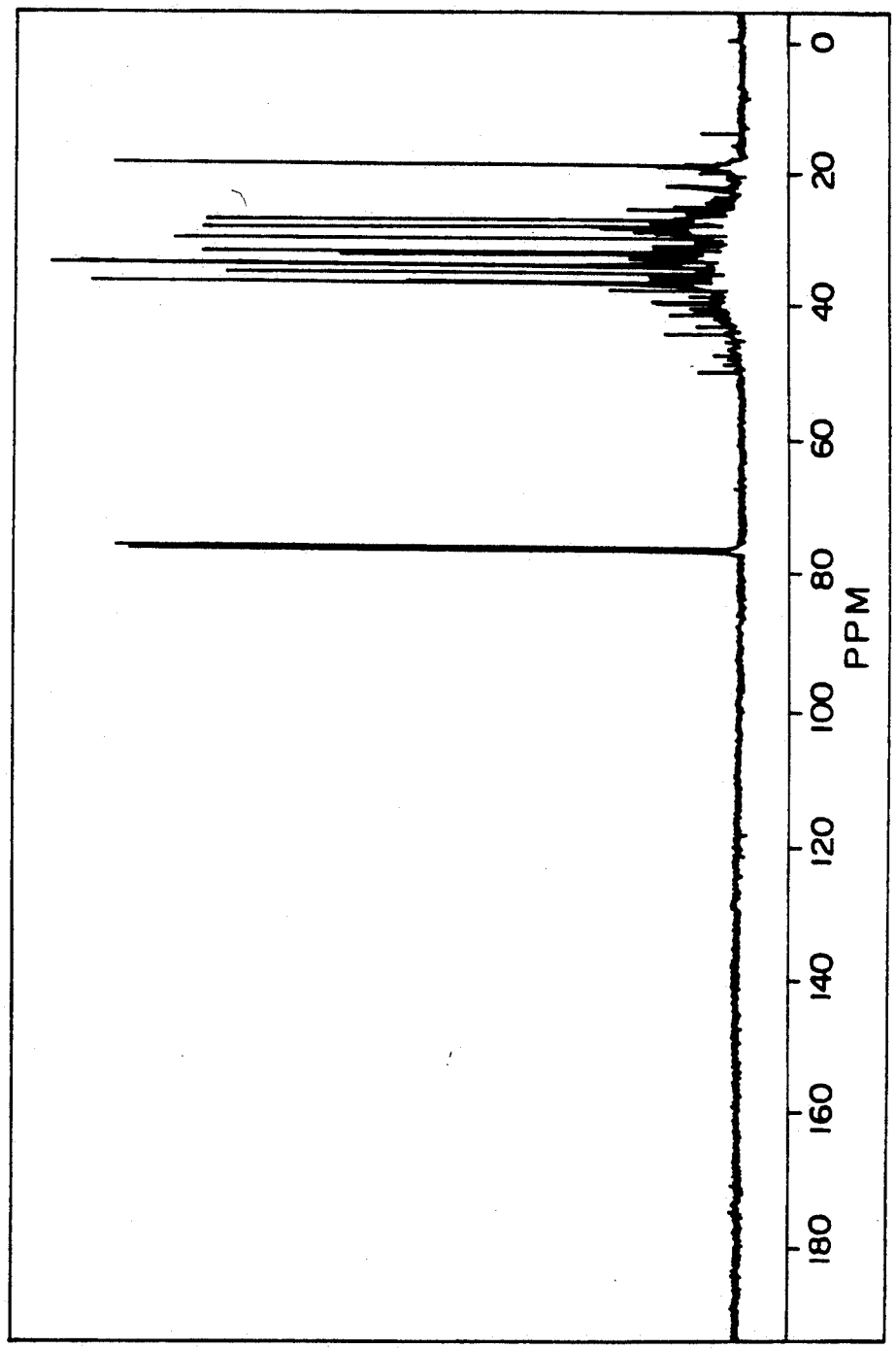
FIG. 20 is a $^{13}$C-NMR chart of the compound obtained in Example 7.
Figure 21:
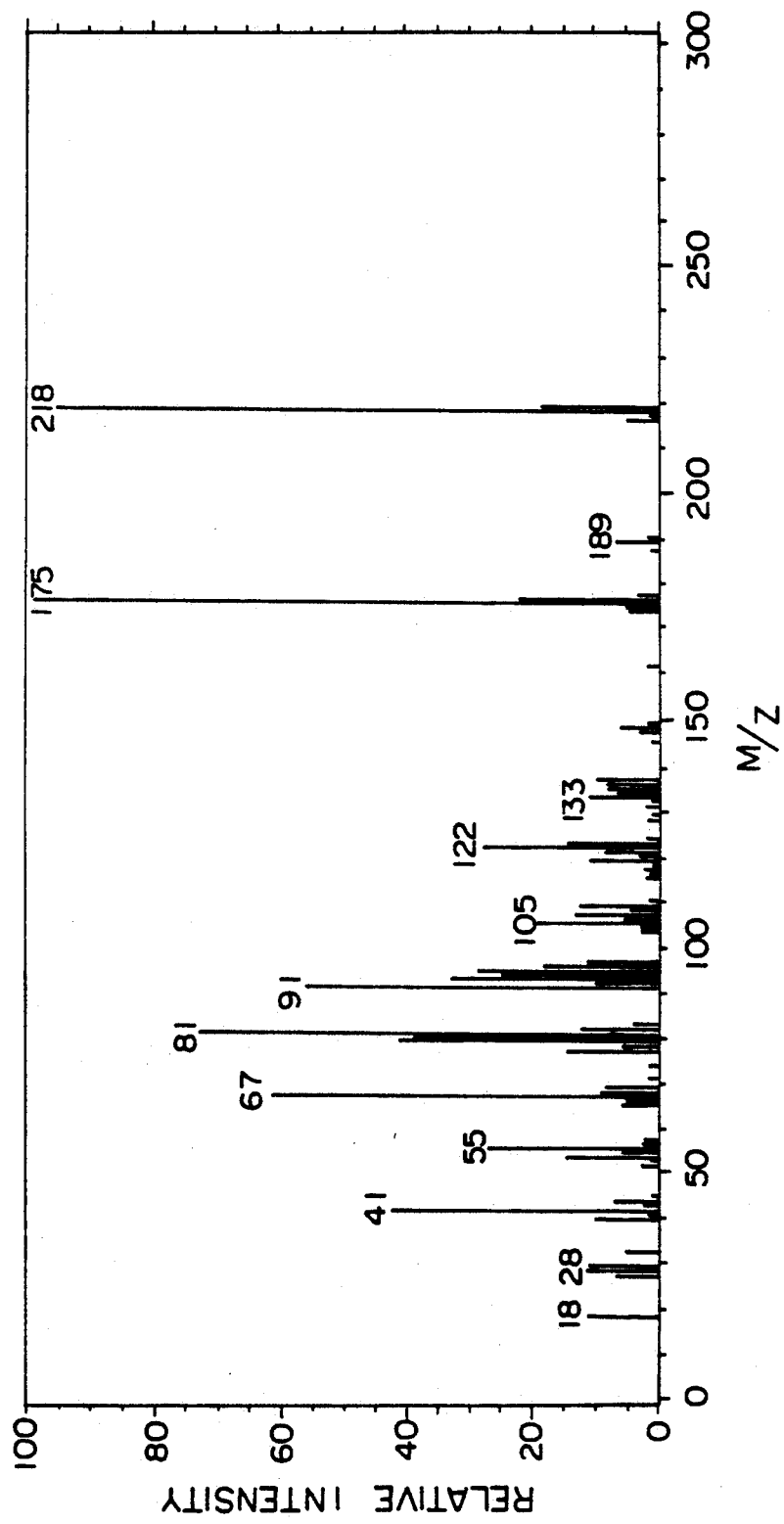
FIG. 21 is a MS chart of the compound obtained in Example 7.

This novel compound was analyzed with $^1$H-NMR, $^{13}$C-NMR and MS and the graphs of these measurements are respectively shown in FIGS. 19 to 21. The traction coefficient of this compound was measured, and the results are shown in FIG. 2.

Further, the reaction product obtained above was found to have the following properties:

| Kinematic viscosity | 24.97 cSt (40° C.) |
|---|---|
|  | 4.420 cSt (100° C.) |
| Viscosity index | 76 |
| Specific gravity (15/4° C.) | 1.0043 |
| Pour point | −47.5° C. |
| Refractive index ($n^{20}_d$) | 1.5267 |

COMPARATIVE EXAMPLE 1

A 5 liter four neck flask was equipped with a thermometer, a dropping funnel, a stirrer and a Dimroth reflux condenser, and 2000 cc of xylene (ratio of weight: o-xylene/m-xylene/p-xylene=24/50/26) and 40 g of aluminum chloride anhydride were placed therein. 227 g of aryl chloride was dropped therein over 8 hours with stirring at room temperature. Then, stirring was continued for another 1.7 hour, the reaction mixture in limited amounts was poured into ice-cold water and the reaction was stopped. The organic layer produced therein was washed twice with 300 ml of 2N HCl aqueous solution, twice with 500 ml of 2N NaOH aqueous solution and twice with 300 ml of water, followed by drying with anhydrous MgSO$_4$. The drying agent was filtered off, fractions of lower polymerization were cut off with distillation and then 385 g of a fraction having a boiling point of 122° to 139° C./2 mmHg was obtained by distillation under reduced pressure.

The analysis of the fraction with NMR, MS and GC showed that the obtained reaction product was a mixture of 1,2-dixylylpropane.

The so obtained reaction product was placed in a 1 liter autoclave and hydrogenated in accordance with substantially the same procedure as in Example 1, with the result that the degree of hydrogenation was 99%. The traction coefficient of the reaction product also was measured, and the results are shown in FIG. 1.

Further, the reaction product obtained above was found to have the following properties:

| Kinematic viscosity | 15.42 cSt (40° C.) |
| --- | --- |
|  | 2.842 cSt (100° C.) |
| Viscosity index | −42 |
| Specific gravity (15/4° C.) | 0.8801 |
| Pour point | −42.5° C. |
| Refractive index ($n^{20}_d$) | 1.4787 |

COMPARATIVE EXAMPLE 2

A 2 liter four neck flask was equipped with the same apparatuses as in Comparative Example 1 above, and 500 ml of methylcyclohexane as the solvent and 156.02 g of isoborneol and 184.01 g of triethylamine both as the starting material were placed therein. With stirring at room temperature, a solution dissolving 146.84 g of cyclohexanecarbonyl chloride in 100 ml of methylcyclohexane was dropped therein over 4 hours. Then, the so obtained mixture was caused to react at 60° C. for 2 hours to complete the reaction.

Next, the mixture was cooled to room temperature, deposited triethylamine hydrochloride was filtered off, the solvent and unreacted starting materials were recovered by a rotary evaporator and 252.51 g of a residual reaction solution was obtained. The so obtained solution was distilled under reduced pressure to obtain 196.48 g of a fraction having a boiling rane of 121° to 131° C./0.2 mmHg. The fraction was analyzed with NMR, IR, GC-MS and the hydrogen flame ionization detector (FID) type gas chromatography, resulting in a finding that isobornylcyclohexanecarboxylate accounted for 99% of said fraction. The traction coefficient of the fraction was measured, and the results are shown in FIG. 2.

Further, the reaction product as obtained above was found to have the following properties:

| Kinematic viscosity | 24.04 cSt (40° C.) |
| --- | --- |
|  | 3.966 cSt (100° C.) |
| Viscosity index | 16 |
| Specific gravity (15/4° C.) | 1.0062 |
| Refractive index ($n^{20}_d$) | 1.4860 |

COMPARATIVE EXAMPLE 3

A 3 liter four neck flask was equipped with a stirrer, a thermometer and a dropping funnel, and 736 g of toluene and 200 g of concentrated sulfuric acid as a catalyst were placed therein and maintained at 2° C. on an ice bath with stirring.

Next, to said flask, a mixed solution of 201 g of dihydrodicyclopentadiene and 92 g of toluene was dropped over 6 hours at the end of which time the reaction solution was at 7° C. Then, stirring was continued for another 1 hour, the reaction solution was transferred to a separating funnel to remove the sulfuric acid layer and the organic layer was washed twice with 200 ml of 1N sodium hydroxide aqueous solution and dried with anhydrous calcium sulfate.

The so obtained mixture was allowed to stand for a day and night, the drying agent was filtered off, the solvent and unreacted starting materials were recovered by a rotary evaporator and 240 g of the residual reaction solution was obtained.

Next, said residual solution was distilled under reduced pressure and 192 g of a fraction having a boiling point of 122° to 125° C./0.2 mmHg was obtained.

The analysis with GC-MS and GC (FID) showed that 99% or more of the obtained reaction product was accounted for by a component having 17 carbon atoms wherein dihydrodicyclopentadiene was added to toluene.

80 g of said fraction and 10 g of 5% by weight ruthenium/active carbon catalyst for hydrogenation (supplied by Japan Engelhard Co., Ltd.) were placed in a 1 liter autoclave, then 200 of methylcyclohexane was added as the solvent and the resulting mixture was hydrogenated under the conditions of a hydrogen pressure of 80 kg/cm$^2$G, a reaction temperature of 160° C. and a reaction time of 5 hours. The mixture was cooled, the catalyst was filtered off, the solvent was removed and the residue was analyzed with a resulting finding that the degree of hydrogenation was 99% or more. The traction coefficient of the reaction product was measured, and the results are shown in FIG. 3.

Further, the reaction product as obtained above was found to have the following properties:

| Kinematic viscosity | 22.67 cSt (40° C.) |
| --- | --- |
|  | 3.789 cSt (100° C.) |
| Viscosity index | 7 |
| Specific gravity (15/4° C.) | 0.9722 |
| Pour point | −35.0° C. |
| Refractive index ($n^{20}_d$) | 1.5112 |

COMPARATIVE EXAMPLE 4

A 2 liter four neck flask was equipped with a thermometer, a Dimroth reflux condenser and a stirrer, and then 800 ml of dicyclopentadiene and 500 ml of 3,3-dimethylacryloyl chloride were placed therein and stirred in an argon stream at 150° C. for 10 hours.

After the mixture was cooled to room temperature, unreacted cyclopentadiene, dicyclopentadiene and 3,3-dimethylacryloyl chloride were distilled off under reduced pressure.

Next, 320 g of 6,6-dimethylbicyclo[2.2.1]hept-2-ene-5-carbonyl chloride was fractionated at a boiling point of 100° to 130° C./30 mmHg.

To 500 ml of a 30% KOH aqueous solution, the so obtained reaction product was added with stirring over 1 hour to hydrolyze and the reaction solution was exothermic to be at 70° C. The reaction solution was cooled to room temperature, then the water layer was fractionated and cooled and concentrated sulfuric acid in limited amounts was added to said water layer with stirring to make pH 1. The isolated organic layer was fractionated and the water layer was extracted twice with 300 ml of ether. The resulting organic layers are collected and dried with Na$_2$SO$_4$, then the solvent was distilled off and 220 g of crude 6,6-dimethyl-bicyclo[2.2.1]hept-2-ene-5-carboxylic acid was obtained.

Next, the so obtained reaction product was transferred to a 1 liter autoclave, 200 ml of methylcyclohexane as the solvent and 30 g of 5% Pd/C as the catalyst were added thereto and the resulting mixture was hydrogenated under hydrogen pressure of 50 kg/cm$^2$G. The so processed mixture began absorbing hydrogen at room temperature, and 10 minutes later when the absorption of hydrogen stopped the temperature was elevated to 100° C. at which the mixture was maintained for 1 hour. Then, hydrogen was found not to be absorbed any longer, the mixture was cooled to room temperature and distilled after the catalyst was filtered off and 180 g of (3,3-dimethylbicyclo[2.2.1]hept-2-yl) carboxylic acid was obtained.

Next, to a 500 ml four neck flask, 150 g of said carboxylic acid was transferred and 140 g of SOCl$_2$ was added thereto to make acid chloride at 50° C. Then, SO$_2$ and HCl gases were found to evolve vigorously. The evolution of gases over, excessive SOCl$_2$ was distilled off under reduced pressure.

Furthermore, in a 1 liter four neck flask, 160 g of isoborneol, 200 ml of toluene and 200 ml of triethylamine were placed and esterified by dropping above synthesized acid chloride therein over 1 hour with stirring. At this time the temperature of the reaction solution exceeded room temperature by 60° C.

Thereafter, the reaction solution was stirred at 90° C. for 2 hours and cooled to room temperature, then the deposited salts were filtered off, fractions of lower polymerization were distilled off and 210 g of desired ester, that is, (3,3-dimethylbicyclo[2.2.1]hept-2-yl)-carboxylic acid-isobornylester was obtained by distillation. The so obtained reaction product was found to have the following properties:

| Kinematic viscosity | 143.4 cSt (40° C.) |
| --- | --- |
| | 8.994 cSt (100° C.) |
| Viscosity index | −38 |
| Specific gravity (15/4° C.) | 1.0194 |
| Pour point | +12.5° C. |
| Refractive index (n$^{20}_d$) | 1.4969 |

This ester has the pour point of 12.5° C., meaning that it is a solid at ambient temperature, far from the use as a traction drive fluid.

COMPARATIVE EXAMPLE 5

In a 1 liter three neck flask, 400 g of α-pinene and 300 ml of methylcyclohexane were placed, and bubbled with dried hydrogen chloride gas for 5 hours at 30° C. with stirring, and then the solvent was distilled off and approximately 500 g of isobornyl chloride was obtained.

Next, in a 1 liter four neck flask wherein the air was replaced with the argon gas, a Grignard reagent was prepared of 25 g of flaky magnesium, 5 drops of 1,2-dibromoethane, 600 ml of ethyl ether and 170 g of isobornyl chloride in accordance with a conventional method.

The so obtained Grignard reagent was bubbled with carbon dioxide for 8 hours, and the reaction mixture was poured into 1 liter of a 30% sodium hydroxide aqueous solution to separate the organic layer from the water layer. Hydrochloric acid was added to the water layer to make the aqueous solution acidic and approximately 90 g of liberated (1,7,7-trimethylbicyclo[2.2.1]hept-2-yl) carboxylic acid was obtained.

Next, in a 500 ml three neck flask, 200 ml of methylcyclohexane, 120 g of camphene, approximately 90 g of carboxylic acid obtained above and 5 ml of concentrated sulfuric acid were placed and stirred at 50° C. for 6 hours, and the reaction mixture was washed with saturated brine and 1N sodium hydroxide aqueous solution and dried with anhydrous magnesium sulfate.

The so processed mixture was allowed to stand for a day and night, then the methylcyclohexane solvent, unreacted camphene and carboxylic acid were distilled off and 85 g of a fraction having a boiling point of 170° to 175° C./0.2 mmHg was obtained by distillation under reduced pressure. However, the fraction or (1,7,7-trimethylbicyclo[2.2.1]hept-2-yl) carboxylic acid isobornyl ester is a solid at room temperature and cannot find its place as a traction drive fluid.

Meanwhile, in above-mentioned Examples and Comparative Examples, the traction coefficient was obtained by measurement with a twin disk machine. The machine was consisted of 2 rollers of same size (having a diameter of 52 mm and a thickness of 6 mm; the roller to be driven was in the shape of a barrel having a curvature radius of 10 mm, while the driving roller was of flat shape without crowning) which contact with each other. One roller was caused to rotate at a constant speed (1500 rpm) and the other at a speed of 1500 rpm to 1750 rpm continuously. A load of 7 kg was applied to contact portion of both the rollers by means of a spring to cause the tangential force, i.e. traction force between them, and thus a traction coefficient was determined by measuring said force. The rollers were made of bearing steel SUJ-2, mirror finished and capable of a maximum Herzian contact pressure of 112 kgf/mm$^2$.

In the testing conducted for the sake of the present invention, the relationship between the traction coefficient and the oil temperature was determined as well by heating the oil tank with a heater, varying the oil temperature from 40° C. to 140° C. and plotting the relationship between the traction coefficient and the oil temperature at a slip ratio of 5%.

What is claimed is:

1. A traction drive fluid composition comprising an effective traction improving amount of a hydrocarbon having a bicyclo octane skeleton selected from the group consisting of

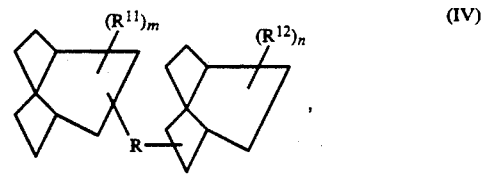

(IV)

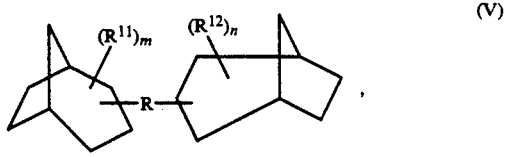

(V)

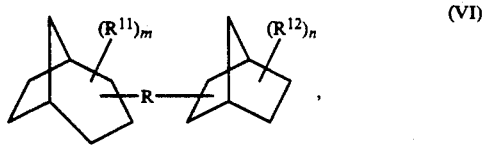

(VI)

-continued

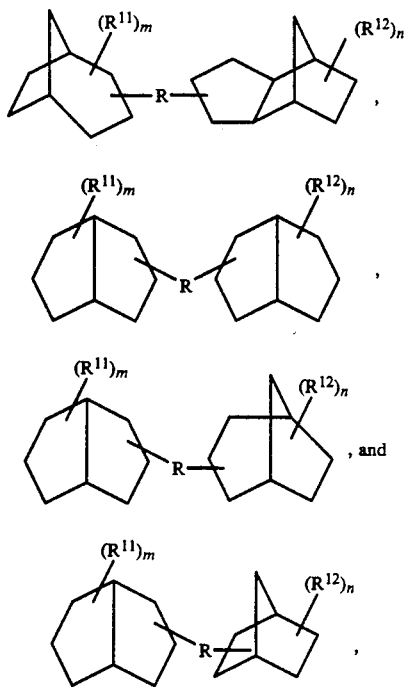

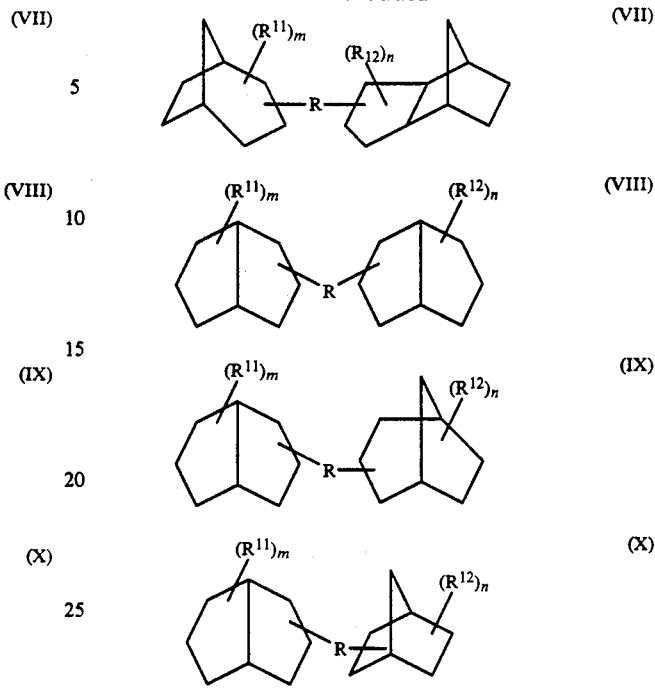

wherein $R^{11}$ and $R^{12}$ each represent a hydrogen atom, a methyl group or an ethyl group, and m and n each represent an integer of 1 to 4; and R represents a single bond or an alkylene group having 1 to 2 carbon atoms which is unsubstituted or substituted with an alkyl group having 1 to 2 carbon atoms.

2. A bicyclo octane compound represented by the following formula (IV), (V), (VI), (VIII), (IX) or (X):

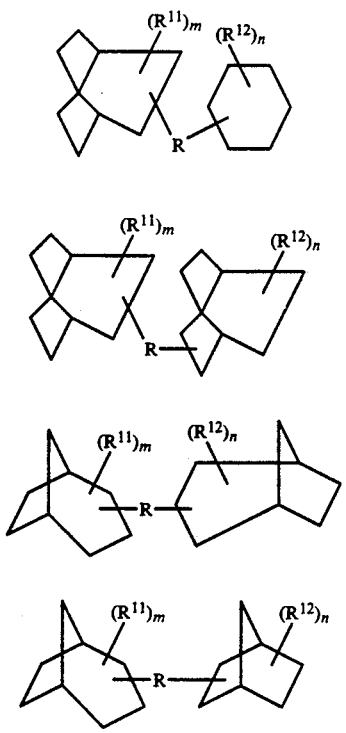

wherein $R^{11}$ and $R^{12}$ each represent a hydrogen atom, a methyl group or an ethyl group, and m and n each represent an integer of 1 to 4; and R represents a single bond or an alkylene group having 1 to 2 carbon atoms which is unsubstituted or substituted with an alkyl group having 1 to 2 carbon atoms.

3. The traction drive fluid composition as claimed in claim 1, wherein the hydrocarbon having a bicyclo octane skeleton is contained in an amount of at least 5% by weight.

4. The traction drive fluid composition as claimed in claim 1, wherein the hydrocarbon having a bicyclo octane skeleton is contained in an amount of at least 30% by weight.

5. The traction drive fluid composition as claimed in claim 1, which further comprises a paraffinic mineral oil, a naphthenic mineral oil, alkylbenzene, polybutene, poly alpha-olefin, 1-cyclohexyl-1-decalyethane, 1,3-dicyclohexyl-3-methylbutane, dicyclohexylpentane, 1,2-bis(methylcyclohexyl)-2-methylpropane, 1,1-bis(-methylcyclohexyl)-2-methylpropane, 2,4-dicyclohexyl-2-methylpentane or 1,3-bis(bicyclo(2,2,1)heptyl)-butane.

6. The traction drive fluid composition as claimed in claim 1, which further comprises an additive selected from the group consisting of an antioxidant, a rust inhibitor, a detergent dispersant, a pour point dispersant, a viscosity index improver, an extreme pressure agent, an antiwear agent, a fatigue preventing agent, an antifoam agent, an oiliness improver and a colorant.

7. The bicyclo octane compound as claimed in claim 2, wherein said compound is selected from the group consisting of 1,1-bis(bicyclo[2.2.2]-2-octyl)-methane, 1,1-bis(bicyclo[2.2.2]-2-octyl)-ethane, bis(bicyclo[2.2.2]-2-octyl), 1-(2-methyl-bicyclo[2.2.2]-2-octyl)-1-(bicyclo[2.2.2]-2-octyl)-methane, 1-(2-methyl-bicyclo8 2.2.2]-2-octyl)-1-(bicyclo[2.2.2]-2-octyl)-ethane, 1-(2, 3-dimethyl-bicyclo[2.2.2]-2-octyl)-1-(3-methyl-bicyclo[2.2.2]-2-octyl)-methane and 1-(2, 3-dimethyl-bicyclo[2.2.2]-2-octyl)-1-(3-methyl-bicyclo[2.2.2]-2-octyl-ethane, 2-(bicyclo[3.2.1]-2-octyl)-bicyclo[3.2.1]octane, 3-(bicyclo[3.2.1]-2-octyl)-bicyclo[3.2.1]octane, bis(bicyclo[3.2.1]-2-octyl), bis(bicyclo[3.2.1]-3-octyl), bis(4-methyl-bicyclo[3.2.1]-2-octyl), bis(4-methyl-bicyclo[3.2.1]-3-octyl), 1-(2-methyl-bicyclo[3.2.1]-2-octyl)-1-(bicyclo[3.2.1]-2-octyl)-methane, 1-(2-methyl-bicyclo[3.2.1]-2-octyl)-1-(bicyclo[3.2.1]-2-octyl)-ethane, 2-(2-methylbicyclo[3.2.1]-2-octyl)-bicyclo[3.2.1]octane, 3-(2-methylbicyclo[3.2.1]-2-octyl)-bicyclo[3.2.1]octane, 2-(4-methylbicyclo[3.2.1]-2-octyl)-bicyclo[3.2.1]octane, 2-(4-methylbicyclo[3.2.1]-3-octyl)-bicyclo[3.2.1]octane, 3-(4-methylbicyclo[3.2.1]-2-octyl)-bicyclo[3.2.1]octane, 3-(4-methylbicyclo[3.2.1]-3-octyl)-bicyclo[3.2.1]octane, 2-(4-methylbicyclo[3.2.1]-2-octyl)-(2-methylbicyclo[3.2.1]octane), 2-(4-methylbicyclo[3.2.1]-3-octyl)-(2-methylbicyclo[3.2.1]octane), 3-(4-methylbicyclo[3.2.1]-2-octyl)-(2-methylbicyclo[3.2.1]octane) and 3-(4-methylbicyclo[3.2.1]-3-octyl)-(2-methylbicyclo[3.2.1]octane), 2-(bicyclo[3.2.1]-2-octyl)-bicyclo[2.2.1]heptane, 2-(2-methyl-bicyclo[3.2.1]-3-octyl)-(2,3-dimethyl-bicyclo[2.2.1]heptane), 2-(2-methyl-bicyclo[3.2.1]-4-octyl)-(2,3-dimethyl-bicyclo[2.2.1]heptane), 2-(2-methylbicyclo[3.2.1]-3-octyl)-(2-methylbicyclo[2.2.1]heptane, 2-(2-methyl-bicyclo[3.2.1]-4-octyl)-(2-methyl-bicyclo[2.2.1]heptane), 2-(2-methyl-bicyclo[3.2.1]-3-octyl)-(3-methylbicyclo[2.2.1]heptane), 2-(2-methyl-bicyclo[3.2.1]-4-octyl)-(3-methylbicyclo[2.2.1]heptane), 1-(2-methyl-bicyclo[3.2.1]-3-octyl)-1-(2-methylbicyclo[2.2.1]-2-heptyl)methane, 1-(2-methylbicyclo[3.2.1]-4-octyl)-1-(2-methylbicyclo[2.2.1]-2-heptyl)methane, 1-(2-methyl-bicyclo[3.2.1]-3-octyl)-1-(2-methylbicyclo[2.2.1]-2-heptyl)ethane, 1-(2-methyl-bicyclo[3.2.1]-4-octyl)-1-(2-methylbicyclo[2.2.1]-2-heptyl)ethane, 1-(2-methyl-bicyclo[3.2.1]-3-octyl)-1-(2-methylbicyclo[2.2.1]-3-heptyl)methane, 1-(2-methyl-bicyclo[3.2.1]-4-octyl)-1-(2-methylbicyclo[2.2.1]-3-heptyl)methane, 1-(2-methyl-bicyclo[3.2.1]-3-octyl)-1-(2-methylbicyclo[2.2.1]-3-heptyl)ethane, 1-(2-methyl-bicyclo[3.2.1]-4-octyl)-1-(2-methylbicyclo[2.2.1]-3-heptyl)ethane, 1-(2-methyl-bicyclo[3.2.1]-3-octyl)-1-(bicyclo[2.2.1]-2-heptyl)methane, 1-(2-methyl-bicyclo[3.2.1]-4-octyl)-1-(bicyclo[2.2.1]-2-heptyl)methane, 1-(2-methyl-bicyclo[3.2.1]-3-octyl)-1-(bicyclo[2.2.1]-2-heptyl)ethane, 1-(2-methyl-bicyclo[3.2.1]-4-octyl)-1-(bicyclo[2.2.1]-2-heptyl)ethane, 1-(bicyclo[3.2.1]-2-octyl)-1-bicyclo[2.2.1]-2-heptyl)methane, 1-(bicyclo[3.2.1]-3-octyl)-1-(bicyclo[2.2.1]-2-heptyl)methane, 1-(bicyclo[3.2.1]-2-octyl)-1-(bicyclo[2.2.1]-2-heptyl)ethane, 1-(bicyclo[3.2.1]-3-octyl)-1-(bicyclo[2.2.1]-2-heptyl)ethane, 3-(bicyclo[3.2.1]-2-octyl)-tricyclo[5.2.1.0$^{2.6}$]decane, 4-(bicyclo[3.2.1]-2-octyl)-tricyclo[5.2.1.0$^{2.40}$]decane, 3-(2-methylbicyclo[3.2.1]-3-octyl)-tricyclo[5.2.1.0$^{2.6}$]decane, 3-(2-methylbicyclo[3.2.1]-4-octyl)-tricyclo]5.2.1.0$^{2.6}$]-decane, 4-(2-methylbicyclo[3.2.1]-3-octyl)-tricyclo[5.2.1.0$^{2.6}$]decane, 4-(2-methylbicyclo[3.2.1]-4-octyl)-tricyclo[5.2.1.0$^{2.6}$]decane, 1-(bicyclo[3.2.1]-2-octyl)-1-(tricyclo[5.2.1.0$^{2.6}$]-3-decyl)methane, 1-(bicyclo[3.2.1]-2-octyl)-1-(tricyclo[5.2.1.0$^{2.6}$]-4-decyl)methane, 1-(bicyclo[3.2.1]-3-octyl)-1-(tricyclo[5.2.1.0$^{2.6}$]-3-decyl)methane, 1-(bicyclo[3.2.1]-3-octyl)-1-(tricyclo[5.2.1.0$^{2.6}$]-4-decyl)methane, 1-(bicyclo[3.2.1]-2-octyl)-1-(tricyclo[5.2.1.0$^{2.6}$]-3-decyl)ethane, 1-(bicyclo[3.2.1]-2-octyl)-1-(tricyclo[5.2.1.0$^{2.6}$]-4-decyl)ethane, 1-(bicyclo[3.2.1]-3-octyl)-1-(tricyclo[5.2.1.0$^{2.6}$]-3-decyl)ethane, 1-bicyclo[3.2.2]-3-octyl)-1-(tricyclo[5.2.1.0$^{2.6}$]-4-decyl)ethane, 2-(bicyclo[3.3.0]-2-octyl)-bicyclo[3.3.0]octane, 3-(bicyclo[3.3.0]-2-octyl)-bicyclo[3.3.0]octane, bis(bicyclo[3.3.0]-2-octyl), bis(bicyclo[3.3.0]-3-octyl), bis(4-methyl-bicyclo[3.3.0]-2-octyl), bis(4-methyl-bicyclo[3.3.0]-3-octyl), 1-(2-methyl-bicyclo[3.3.0]-2-octyl)-1-(bicyclo[3.3.0]-2-octyl)-methane, 1-(2-methyl-bicyclo[3.3.0]-2-octyl)-1-(bicyclo[3.3.0]-2-octyl)-ethane, 2-(2-methylbicyclo[3.3.0]-2-octyl)-bicyclo[3.3.0]octane, 3-(2-methylbicyclo[3.3.0]-2-octyl)-bicyclo[3.3.0]octane, 2-(4-methylbicyclo[3.3.0]-2-octyl)-bicyclo[3.3.0]octane, 2-(4-methylbicyclo[3.3.0]-3-octyl)-bicyclo[3.3.0]octane, 3-(4-methylbicyclo[3.3.0]-2-octyl)-bicyclo[3.3.0]octane, 3-(4-methylbicyclo[3.3.0]-3-octyl)-bicyclo[3.3.0]octane, 2-(4-methylbicyclo[3.3.0]-2-octyl)-(2-methylbicyclo[3.3.0]octane), 2-(4-methylbicyclo[3.3.0]-3-octyl)-(2-methylbicyclo[3.3.0]octane), 3-(4-methylbicyclo[3.3.0]-2-octyl)-(2-methylbicyclo[3.3.0]octane), 3-(4-methylbicyclo[3.3.0]-3-octyl)-(2-methylbicyclo[3.3.0]octane), 2-(bicyclo[3.3.0]-2-octyl)-bicyclo[3.2.1]octane, 3-(bicyclo[3.3.0]-2-octyl)-bicyclo[3.2.1]octane, 1-(2-methylbicyclo[3.3.0]-2-octyl)-1-(bicyclo[3.2.1]-2-octyl)methane, 1-(2-methyl-bicyclo[3.3.0]-2-octyl)-1-(bicyclo[3.2.1]-2-octyl)-ethane, 2-(2-methylbicyclo[3.3.0]-2-octyl)-bicyclo[3.2.1]-octane, 3-(2-methylbicyclo[3.3.0]-2-octyl)-bicyclo[3.2.1]octane, 2-(4-methylbicyclo[3.3.0]-2-octyl)-bicyclo[3.2.1]octane, 2-(4-methylbicyclo[3.3.0]-3-octyl)-bicyclo[3.2.1]octane, 3-(4-methylbicyclo[3.3.0]-2-octyl)-bicyclo[3.2.1]octane, 3-(4-methylbicyclo[3.3.0]-3-octyl)-bicyclo[3.2.1]octane, 2-(4-methylbicyclo[3.3.0]-2-octyl)-(2-methylbicyclo[3.2.1]octane), 2-(4-methylbicyclo[3.3.0]-3-octyl)-(2-methylbicyclo[3.2.1]octane), 3-(4-methylbicyclo[3.3.0]-2-octyl)-(2-methylbicyclo[3.2.1]octane) and 3-(4-methylbicyclo[3.3.0]-3-octyl)-(2-methylbicyclo[3.2.1]octane, 2-(bicyclo[3.3.0]-2-octyl)-bicyclo[2.2.1]heptane, 2-(2-methyl-bicyclo[3.3.0]-3-octyl)-(2,3-dimethyl-bicyclo[2.2.1]heptane), 2-(2-methyl-bicyclo[3.3.0]-4-octyl)-(2,3-dimethylbicyclo[2.2.1]heptane), 2-(2-methylbicyclo[3.3.0]-3-octyl)-(2-methylbicyclo[2.2.1]heptane), 2-(2-methyl-bicyclo[3.3.0]-4-octyl)-(2-methylbicyclo[2.2.1]heptane, 2-(2-methyl-bicyclo[3.3.0]-3-octyl)-(3-methylbicyclo[2.2.1]heptane), 2-(2-methyl-bicyclo[3.3.0]-4-octyl)-(3-methylbicyclo[2.2.1]heptane), 1-(2-methyl-bicyclo[3.3.0]-3-octyl)-1-(2-methylbicyclo[2.2.1]-2-heptyl)methane, 1-(2-methylbicyclo[3.3.0]-4-octyl)-1-(2-methylbicyclo[2.2.1]-2-heptyl)methane, 1-(2-methyl-bicyclo[3.3.0]-3-octyl)-1-(2-methylbicyclo[2.2.1]-2-heptyl)ethane, 1-(2-methyl-bicyclo[3.3.0]-4-octyl)1-(2-methylbicyclo[2.2.1]-2-heptyl)ethane, 1-(2-methyl-bicyclo[3.3.0]-3-octyl)-1-(2-methylbicyclo[2.2.1]-3-heptyl)methane, 1-(2-methyl-bicyclo[3.3.0]-4-octyl)-1-(2-methylbicyclo[2.2.1]-3-heptyl)methane, 1-(2-methyl-bicyclo[3.3.0]-3-octyl)-1-(2-methylbicyclo[2.2.1]-3-heptyl)ethane, 1-(2-methyl-bicyclo[3.3.0]-4-octyl)-1-(2-methylbicyclo[2.2.1]-3-heptyl)ethane, 1-(2-methyl-bicyclo[3.3.0]-3-octyl)-1-(bicyclo[2.2.1]-2-heptyl)methane, 1-(2-methyl-bicyclo[3.3.0]-4-octyl)-1-(bicyclo[2.2.1]-2-heptyl)methane, 1-(2-methyl-bicyclo[3.3.0]-3-octyl)-1-(bicyclo[2.2.1]-2-heptyl)ethane, 1-(2-methyl-bicyclo[3.3.0]-4-octyl)-1-(bicyclo[2.2.1]-2-heptyl)ethane, 1-(bicyclo[3.3.0]-2-octyl)-1-(bicyclo[2.2.1]-2-heptyl)methane, 1-(bicyclo[3.3.0]-3-octyl)-1-(bicyclo[2.2.1]-2-heptyl)methane, 1-(bicyclo[3.3.0]-2-octyl)-1-(bicyclo[2.2.1]-2-heptyl)ethane and 1-(bicyclo[3.3.0]-3-octyl)-1-(bicyclo[2,2,1]-2-heptyl)ethane.

* * * * *

UNITED STATES PATENT AND TRADEMARK OFFICE
CERTIFICATE OF CORRECTION

PATENT NO. : 5,283,384

DATED : February 1, 1994

INVENTOR(S) : ABE et al

It is certified that error appears in the above-identified patent and that said Letters Patent is hereby corrected as shown below:

```
Title Page, left column, [56], References Cited, under
U.S. PATENT DOCUMENTS, insert
         --3,411,369   11/1968   Hammann et al--.

Column 23, line 38 (Claim 2): after "(VI)," insert
         --(VII)--.

Column 23, lines 40-45 (Claim 2):  delete all of the
         subject matter on these lines.
```

Signed and Sealed this

Third Day of September, 1996

Attest:

BRUCE LEHMAN

Attesting Officer     Commissioner of Patents and Trademarks